United States Patent
Nikolskiy et al.

(10) Patent No.: US 10,327,867 B2
(45) Date of Patent: Jun. 25, 2019

(54) ARCH FORM PLACEMENT FOR DENTAL RESTORATION DESIGN

(71) Applicant: James R. Glidewell Dental Ceramics, Inc., Newport Beach, CA (US)

(72) Inventors: Sergey Nikolskiy, Coto de Caza, CA (US); Shawn Andrews Ramirez, Santa Ana, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 586 days.

(21) Appl. No.: 14/834,299

(22) Filed: Aug. 24, 2015

(65) Prior Publication Data
US 2016/0242880 A1    Aug. 25, 2016

Related U.S. Application Data

(60) Provisional application No. 62/120,567, filed on Feb. 25, 2015.

(51) Int. Cl.
| A61C 13/00 | (2006.01) |
| A61C 5/77 | (2017.01) |
| A61C 7/00 | (2006.01) |

(52) U.S. Cl.
CPC ............ *A61C 5/77* (2017.02); *A61C 7/002* (2013.01); *A61C 13/0004* (2013.01)

(58) Field of Classification Search
CPC ...... A61C 13/0004; A61C 9/004; A61C 7/002
See application file for complete search history.

(56) References Cited

U.S. PATENT DOCUMENTS

| 7,740,476 B2 | 6/2010 | Rubbert et al. |
| 8,386,061 B2 | 2/2013 | Violante et al. |
| 8,594,820 B2 | 11/2013 | Manai et al. |
| 8,718,982 B2 | 5/2014 | Fisker et al. |
| 8,727,776 B2 | 5/2014 | Mehl |
| 2004/0029068 A1* | 2/2004 | Sachdeva ............... A61C 7/00 433/24 |
| 2008/0248443 A1* | 10/2008 | Chishti .................. A61C 7/00 433/24 |
| 2012/0072177 A1* | 3/2012 | Manai .................. A61C 11/00 703/1 |
| 2015/0111177 A1* | 4/2015 | Fisker ................. A61C 13/01 433/196 |
| 2016/0310244 A1* | 10/2016 | Fisker ................. A61C 9/004 |

FOREIGN PATENT DOCUMENTS

| JP | 2013128694 A | 7/2013 |
| JP | 2013537077 A | 9/2013 |
| WO | 20120354M A2 | 3/2012 |
| WO | 2012055420 A1 | 5/2012 |

* cited by examiner

*Primary Examiner* — Douglas King
(74) *Attorney, Agent, or Firm* — Charles Fowler

(57) ABSTRACT

A computer-implemented method of designing a dental restoration at a display includes providing a virtual three dimensional representation of at least a portion of the patient's dental situation. The method includes displaying a library arch form in an alignment with the virtual three dimensional representation of the portion of the patient's dentition. The library arch form includes a pair of two virtual library teeth packing to each other. The method also includes in response to a parametric change of one of the two virtual library teeth, moving the other virtual library tooth to keep packing to the changed virtual library tooth.

16 Claims, 25 Drawing Sheets

ARCH FORM PLACEMENT FOR DENTAL RESTORATION DESIGN

CROSS-REFERENCE TO RELATED APPLICATION(S)

This application claims priority under 35 U.S.C. § 119(e) to U.S. Provisional Patent Application Ser. No. 62/120,567, titled "Arch Form Placement for Dental Restoration Design," filed Feb. 25, 2015, which is incorporated herein by reference in its entirety.

TECHNICAL FIELD

The disclosure relates generally to the field of dental restoration design, and specifically to arch form placement for dental restoration design.

BACKGROUND

Recently, CAD/CAM dentistry (Computer-Aided Design and Computer-Aided Manufacturing in dentistry) has provided a broad range of dental restorations, including crowns, veneers, inlays and onlays, fixed bridges, dental implant restorations, and orthodontic appliances. In a typical CAD/CAM based dental procedure, a treating dentist can prepare the tooth being restored either as a crown, inlay, onlay or veneer. The prepared tooth and its surroundings are then imaged by a three dimensional (3D) imaging camera and uploaded to a computer for design. Alternatively, a dentist can obtain an impression of the tooth to be restored and the impression may be scanned directly, or formed into a model to be scanned, and uploaded to a computer for design.

Current dental restoration design programs may display the 3D image or the scanned model on the computer as a virtual 3D dental representation of the patient's dentition. The design programs may also allow users to design dental restoration based on the 3D image or the scanned model. When more than one tooth have been imaged or scanned, the users are only allowed to move or adjust the teeth individually. That is, when the users move or scale one tooth, other teeth next to it will not change accordingly, which causes some inconvenience and inefficiency for the design.

SUMMARY

A computer-implemented method of designing a dental restoration at a display is disclosed. Embodiments of the method comprise providing a virtual three dimensional representation of at least a portion of the patient's dental situation. The embodiments of the method also comprise displaying a library arch form in an alignment with the virtual three dimensional representation of the portion of the patient's dentition. The library arch form includes a pair of two virtual library teeth packing to each other. The embodiments of the method further comprises in response to a parametric change of one of the two virtual library teeth, moving the other virtual library tooth to keep packing to the changed virtual library tooth.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

DETAILED DESCRIPTION

Figure 1A:
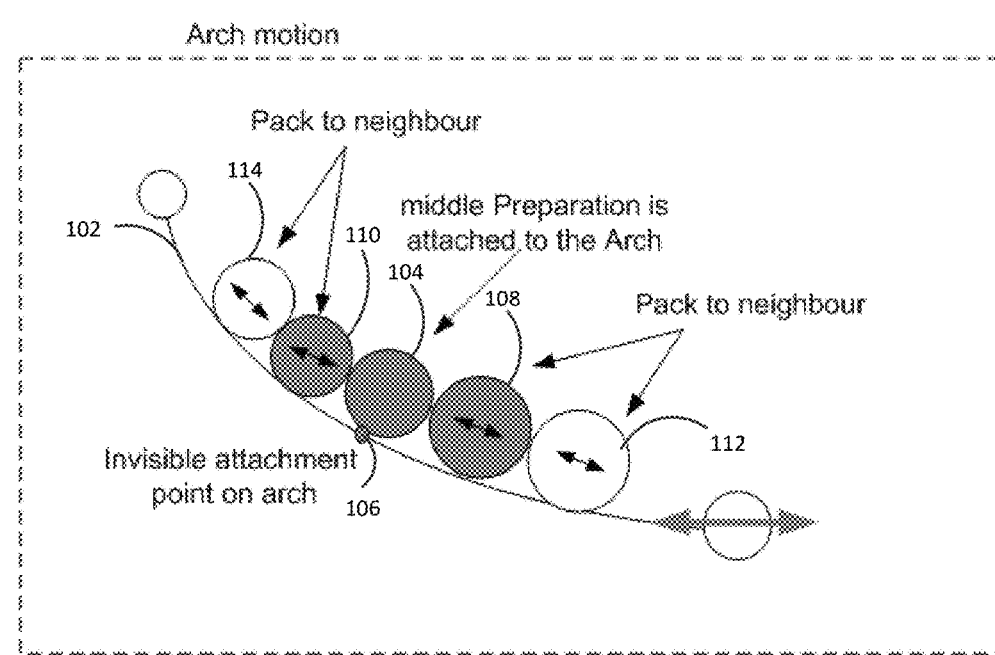
FIGS. 1A-1B are graphic representations showing mesial packing according to one embodiment.

The Figures (FIGS.) and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

Exemplary embodiments of methods and systems for designing dental restorations are described herein. The computer-implemented methods of designing dental restorations described herein use an electronic image of at least a portion of a patient's oral situation as a starting point for the design process. In some embodiments, the electronic image is obtained by a direct intraoral scan of the patient's teeth. This will typically take place, for example, in a dental office or clinic and be performed by a dentist or dental technician. In other embodiments, the electronic image is obtained indirectly by scanning an impression of the patient's teeth, by scanning a physical model of the patient's teeth, or by other methods known to those skilled in the art. This will typically take place, for example, in a dental laboratory and be performed by a laboratory technician. Accordingly, the methods described herein are suitable and applicable for use in chair side, dental laboratory, or other environments. Using the electronic image, a computer-implemented dental restoration design system is used to design a suitable dental restoration and to provide instructions to a restoration fabrication machine, e.g., a mill. The fabrication machine is then used to produce the dental restoration, which may then be installed into the patient's mouth by a dentist.

In one embodiment, a plurality of scans (e.g., 3-5 scans per quadrant) is performed in order to obtain a suitable image of the patient's anatomy. For example, an occlusal, lingual, and buccal scan may be taken of both the preparation and the opposing jaws. Then, a single scan with the jaws in occlusion may be taken from the buccal perspective to establish the proper occlusion relationship between the preparation jaw and the opposing jaw. Additionally, in some embodiments, interproximal scans are added to capture the contact areas of neighboring teeth. Once the scanning process is completed, a scanning system (not shown in FIGS) will assemble the plurality of scans into a digital model (also referred to as a "scanned model" or "scanned dental model" herein) of the preparation tooth and its surrounding and opposing teeth. The scanned model can be used to design a restoration to be used on the preparation tooth. For example, a dental restoration design program may process and display the scanned model in a user interface on a user device. A user (e.g., a design technician) operating on the user device can view the scanned dental model and design a dental restoration based on the scanned model.

In one embodiment, the dental restoration design program may provide a restoration proposal to the user based on the scanned model before the user starts doing manual design. For example, the dental restoration design program can search a tooth library for the library tooth that best matches the neighboring dentition of the preparation tooth in the scanned model and position it naturally, taking into consideration the natural structure of the arch form within which the library tooth is located. In such a process, the dental restoration design program may perform an initial placement of the arch form of library tooth based on the position of the preparation tooth, the buccal direction and the occlusal direction. The dental restoration design program may also fit the arch form of the library tooth to the scanned model based on certain criteria. In addition, the dental restoration design program may improve the position of each individual tooth in the arch form to be aligned to the scanned model.

The user can also place an arch form of the library teeth and fit it to the scanned model of the preparation tooth. In one embodiment, the user may be shown by the dental restoration design program a proposal of the arch form placement and adjust the placement of the arch form manually. During both of the proposal stage performed by the design program and the manual design stage conducted by the user, a mesial packing feature can be added to the design, for example, as shown in FIGS. 1A-2F.

Mesial Packing

In one embodiment, mesial packing between two or more objects can be described as: when an object (e.g., a crown, a tooth in a bridge, a tooth for implant, partial denture, etc.) is pushed into a neighboring object, the neighboring object performs collision. For example, the neighboring object is moved in position to keep packing to the object pushed into it. Furthermore, mesial packing also indicates that the objects can be changed in any one or more associated parameters to pack together if there exists a distance larger than a limit between one another. For example, the objects may be changed in position or size to be within the limit of the distance between each other. In one embodiment, the distance between two objects can be the closest point to point distance along an arch form consisting of the two objects. In other embodiments, the distance can be calculated using any other suitable methods known to those of skill in the art. The limit of the value of the distance can be zero, or any other pre-defined values suitable to different types of scenarios (e.g., dental restoration design). For example, when there is a distance larger than zero between two objects in the arch form, the two objects are changed in position or dimension to pack to each other. In one embodiment, the limit of the distance between two packing objects can be pre-defined by a user or an administrator of the dental restoration design program.

The associated parameters of an object can include, but not be limited to, position, orientation, size, shape, etc. In one embodiment, with the mesial packing effect, a parametric change of one object can cause its neighboring object to also change parametrically to keep packing to the changing object. A parametric change is a change of an object in one of those associated parameters. For example, an object may be changed in position. The object can be moved along any direction. An object may also be changed in orientation. For example, the object can be rotated in any direction. An object may be changed in size. For example, the object can be scaled or resized to a larger size (e.g., enlarged) or a smaller size (e.g., shrunk). The rescaling and resizing of the object may be concentric or not concentric. An object may also be changed in shape or contour. For example, an object may be replaced by another object with a different shape.

Any other associated parameters with an object that can be changed may also be recognized by those of skill in the art.

The mesial packing function can be applied to any types of dental restorations known to those of skill in the art. For example, the applications may include, but not be limited to, crown, bridge, implant, partial denture, veneer, inlay, onlay, orthodontic appliances, etc. In the embodiments of crown or bridge design, teeth in an arch form may collide with one another if any one of the teeth is moved or resized; and the teeth may be moved or resized to pack together if the distance between any two neighboring teeth becomes larger than a limit (e.g., more than zero) due to movement or resizing (or scaling) of any one of the two teeth. The movement and resizing can be performed in both directions along the arch form.

Figure 1B:
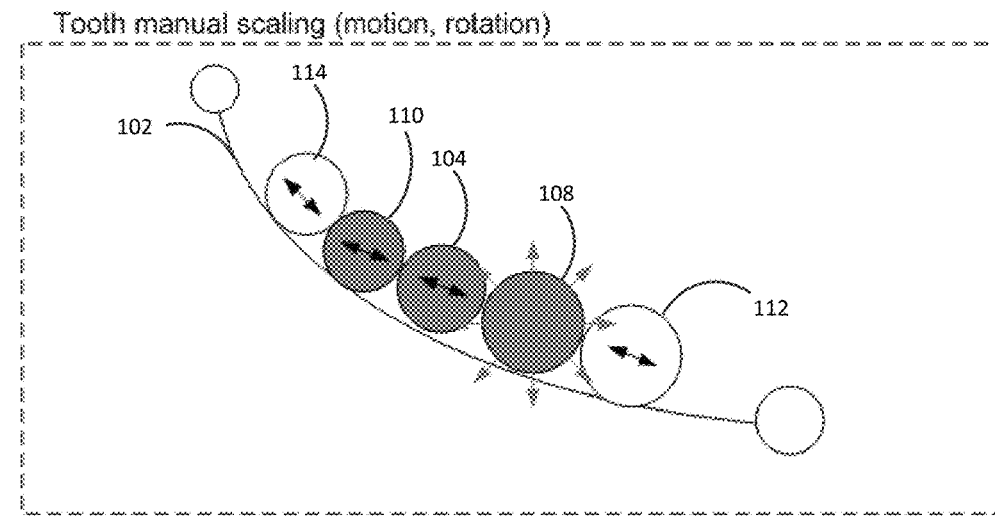

Referring now to FIGS. 1A-1B, mesial packing in arch motion and manual scaling of tooth are depicted according to one embodiment. Referring to FIG. 1A, a graphic representation 100 shows mesial packing in arch motion according to one embodiment. Element 102 is a graphic representation of an arch. Element 104 is a graphic representation of a preparation tooth that is attached to the arch 102 at an invisible attachment point 106 on the arch 102. Elements 108, 110, 112, 114 are graphic representations of neighboring teeth to the preparation tooth 104. In the depicted embodiment, the teeth 108, 110, 112, 114 can move in both directions along the arch 102 to pack to one another, as depicted by the double arrows on these teeth. The preparation tooth 104 is fixed in its position on the arch 102 and may only expand or shrink to keep packing when other teeth in the arch form are moving, since it's the center of the arch form. In one embodiment, if the number of teeth in the arch is an odd integer, the tooth at the center of the arch form is fixed. In the depicted embodiment, there are five teeth in the arch form and the preparation tooth 104 is in the center and therefore is fixed. In other embodiments, the number of the teeth in an arch may be an even integer. In such embodiments, the two teeth in the middle of the arch can be fixed in their positions respectively and may only expand or shrink to keep packing to neighboring teeth. For example, the two middle teeth may be resized in the same amount.

In other embodiments, all teeth in an arch form (e.g., preparation teeth, non-preparation teeth) can move along the arch to stay packing to one another. For example, when any of the teeth 104, 108, 110, 112, 114 is moved or resized, the other teeth move or resize to pack to one another within a certain distance (such as zero). For example, when the preparation tooth 104 is moved from another position to the attachment point 106, the neighboring teeth 108, 110, 112, 114 all move to pack to one another. In another example, when the tooth 108 is moved to another position, its neighbor tooth 112 moves to keep packing to the tooth 108 (e.g., with zero contact distance to the tooth 108). The preparation tooth 104 can expand or shrink (without moving its position in the arch 202) to keep packing to the moving tooth 108. In other embodiments, the preparation tooth 104 can also move to pack to the moving tooth 108. In addition, the teeth 110, 114 may also move to pack to corresponding neighbor teeth 104, 110, respectively, for example, to be with zero contact distance to them respectively.

Referring to FIG. 1B, a graphic representation 150 shows mesial packing in scaling of tooth according to one embodiment. In the depicted embodiment, the tooth 108 is scaled to a larger size and therefore pushed to its neighboring teeth 104, 112. The scaling of the tooth 108 radiate outward from the center point of the tooth 108. Thus, its neighboring teeth 104, 112 perform collision and move along the arch 102 so that the neighboring teeth 104, 112 are still within zero contact distance from the tooth 108. In some embodiments, besides moving, the neighboring teeth 104, 112 may also rotate in a clockwise or counter-clockwise direction along the arch 102 to keep contact with the resized tooth 108. Furthermore, the tooth 110 neighbor to the tooth 104, and the tooth 114 next to the tooth 110 also move along the arch 102, as if they are pushed by the teeth 104, 110, respectively. Due to mesial packing, the teeth 110, 114 stay packing to the neighboring teeth 104, 110, respectively.

In the depicted embodiments of FIGS. 1A-1B, these teeth 112, 108, 104, 110, 114 can be virtual library teeth forming the arch form 102. One or more of the virtual library teeth of the arch form 102 can be snapped (or anchored) to a fixed status (e.g., in a fixed position, orientation, size, shape, or any combination thereof). In one embodiment, a dental restoration design program can snap the virtual library tooth to scanned dentition data of the patient. In another embodiment, a dental restoration design program may allow the user to snap the virtual library tooth 112 or 114, or both. For example, the user can click and drag the end virtual library tooth 112, 114 to snap it to any fixed position and in any orientation, size and/or shape, not necessarily matching to the scan data. In one embodiment, the preparation tooth or bridge teeth cannot be snapped by a user. The neighboring teeth of the preparation tooth or the bridge can be snapped. That a tooth or object is snapped to a fixed status (e.g., in a fixed position, orientation, size, shape, or any combination thereof) can be referred to as that the tooth or object is snapped or the tooth or object is anchored.

In one embodiment, if the end library tooth 112 is snapped to the scan data and anchored (e.g., fixed in position, size and posture), when the user moves any of the rest teeth 108, 104, 110, 114, the other rest teeth may be moved or resized by the software system to make all teeth in the arch form 102 pack to one another. For example, if the tooth 112 is anchored, when the user moves the tooth 114 to left or right along the arch 102, the tooth 110 is moved or resized (e.g., expanded or shrunk) to pack to the tooth 114. Further, the other teeth 104, 108 may also be moved or resized to pack to their neighboring teeth. In one embodiment, the in-between teeth 110, 104, 108 may be resized (e.g., enlarged or shrunk) in the same amount to pack to their neighboring teeth respectively.

The teeth will behave similarly when the other end library tooth 114 is snapped or anchored. In one embodiment, if the tooth 114 is anchored, when the user moves the tooth 112 to right along the arch 102, the tooth 108 either moves to right or expands in size to pack to the tooth 112. The tooth 104, accordingly, either moves to right or expands in size to pack to the tooth 108. The tooth 110 expands to pack to both of the tooth 104 and the tooth 114. In other embodiments, the design program may expand the tooth 108 large enough to pack to the moving tooth 112 without moving or expanding the other two teeth 104, 110. In yet other embodiments, the design program may expand any one or all of the teeth 108, 104, 110 in between the anchored tooth 114 and the moving tooth 112 to make all teeth in the arch form 102 pack to one another. Other embodiments of how the arch form (or teeth) behaves where one end is anchored and one of the other teeth is moved or resized to keep all teeth in the arch form packing to one another may also be recognized by those of skill in the art. In one embodiment, when the user moves the tooth 110 next to the anchored tooth 114 dramatically enough, in order to pack to the moving tooth 110 the anchored tooth 114 may move away from the anchored position or resize to be different from the scan data and the anchor of the tooth 114 may thus be broken.

If both of the end teeth 112, 114 are snapped or anchored, when the user moves or scales (or resizes) any one of the teeth 110, 104, 108 (between the two end teeth 112, 114), the other in-between teeth also resize to keep all teeth in the arch form 102 packing to one another. For example, if both teeth 112, 114 are anchored, when the user expands the tooth 104, the other in-between teeth 108, 110 may shrink to pack to both their neighboring teeth 112 and 104, 114 and 104, respectively. In the case of both end teeth anchored, if the user resizes the tooth 108, the other two in-between teeth 104, 110 may move or resize to make all teeth in the arch form 102 to pack to their neighboring teeth. In some embodiments, not all of the other in-between teeth changes in size or position to make all teeth in the arch form pack to one another. For example, the design program may change any number of the in-between teeth in size or position to make all teeth in the arch form keep packing to one another. Other embodiments of how the arch form (or teeth) behaves where both ends are anchored and one of the in-between teeth is moved or resized may also be recognized by those of skill in the art.

Figure 1C:
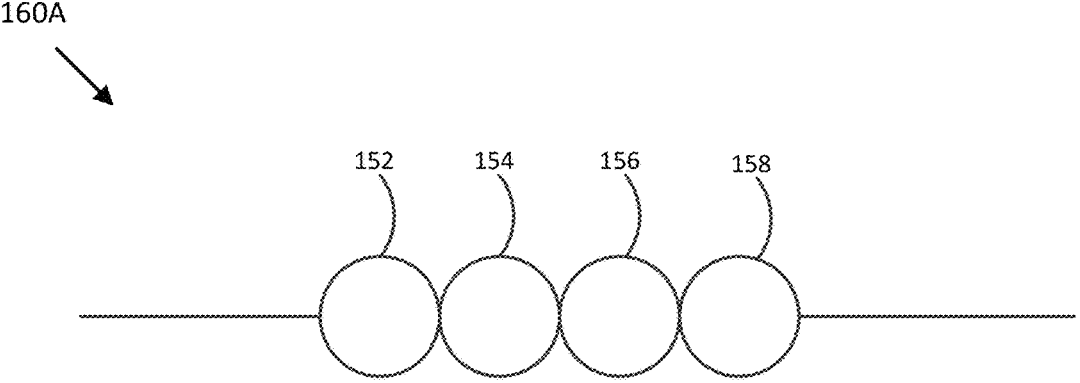
FIG. 1C is graphic representations showing mesial packing with free objects according to one embodiment.
Figure 1C:
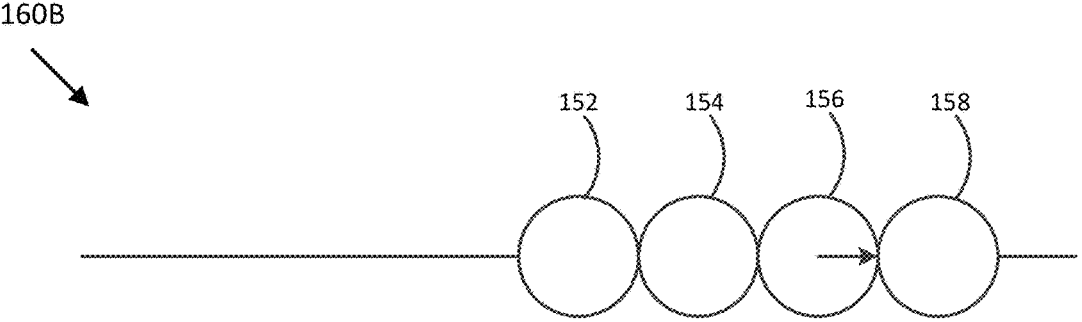
Figure 1C:
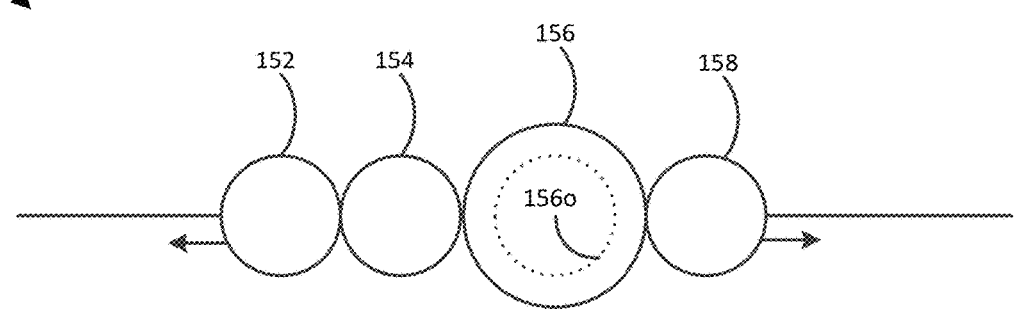
Figure 1D:
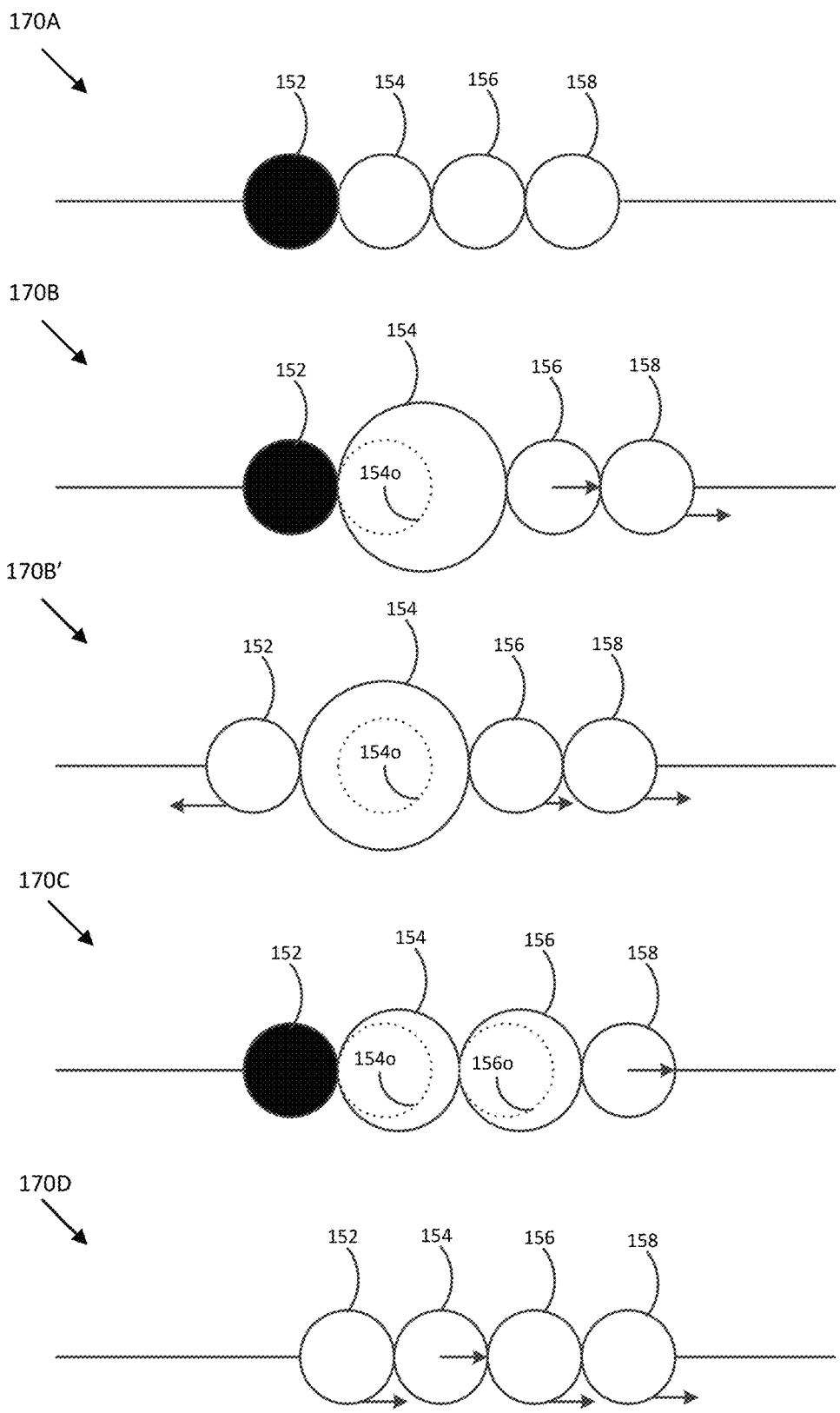
FIG. 1D is graphic representations showing mesial packing with one end object anchored according to one embodiment.
Figure 1E:
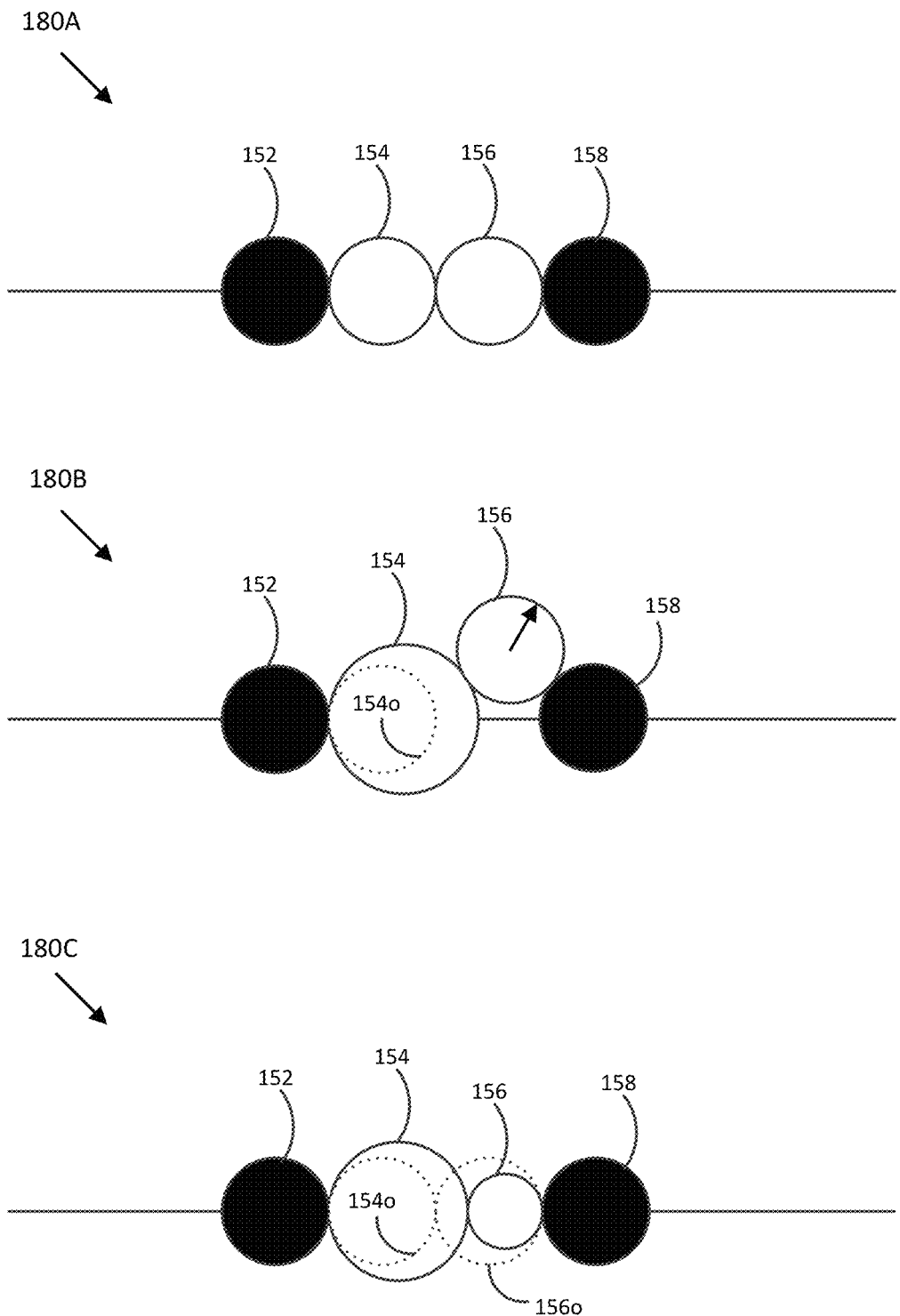
FIG. 1E is graphic representations showing mesial packing with both end objects anchored according to one embodiment.

These behaviors are described in further detail and in many embodiments with references to FIGS. 1C-1E. Referring now to FIG. 1C, depicted are graphic representations 160A-160C showing mesial packing with free objects according to one embodiment. Elements 152, 154, 156, 158 are graphic representations of objects composing an arch form. For example, the objects 152, 154, 156, 158 can include, but not be limited to, a tooth crown, a tooth in a bridge, a tooth for implant, partial denture, etc. In the depicted graphic representation 160A, the objects 152, 154, 156, 158 in the arch form are packed to each other, e.g., within a certain distance (such as zero). The objects 152, 154, 156, 158 are free to move since none of them are snapped or anchored to a fixed position.

In the graphic representation 160B, the object 156 is moved to right along the arch form, as depicted by the arrow on it. According to the mesial packing effect, the other objects 152, 154, 158 are all moved to the right along the arch form to keep packing to their respective neighboring objects. In the graphic representation 160C, the object 156 is resized (e.g., enlarged) to a larger size than the old one's 156o. Responsively, all the other objects in the arch form 152, 154, 158 are moved away by the software to accommodate the enlarged object 156. As a result, all the objects 152, 154, 156, 158 in the arch form are still packed to each other after being changed in position or size.

FIG. 1D is graphic representations 170A, 170B, 170C, 170D showing mesial packing with one end object anchored according to one embodiment. In the depicted embodiments, the end object 152 is snapped or anchored to a fixed status (e.g., position, size, etc.), as shown in dark. In the graphic representation 170A, the objects 152, 154, 156, 158 compose an arch form. In the graphic representation 170B, the object 156 may be moved to the right along the arch form. Accordingly, the object 158 is also moved to the right along the arch form since it is free to move. In contrast, since the object 154 is connected to the anchored object 152, moving the object 154 cannot make it pack to the object 152. Therefore, the object 154 is resized (e.g., enlarged) to make up the distance caused by the moving of its neighboring object 156. The resized object 154 is larger than the old one 154o. By resizing, the object 154 can still pack to its both neighboring objects 152, 156.

In another scenario shown in graphic representation 170B', the object 154 may be resized (e.g., enlarged) firstly by a user to a bigger size than the old one's 154o. In the depicted embodiment, the object 154 enlarges concentrically. That is, the enlarged object 154 is concentric with the old one 154o. Responsive to the enlargement of the object 154, the objects 156, 158 are moved to the right along the arch form to make room for the enlarged object 154, while still packing to the object 154. The anchored object 152 moves to the left along the arch form to make room for the enlarged object 154 in order to pack to the object 154. Therefore, the anchoring of the object 152 is broken after it moves. The fixed status of the object 152 is lost. In another embodiment, the anchored object 152 may be not moved, but still stay in the anchoring status. For example, the object 154 enlarges to the right side when it is resized by the user. Therefore the anchored object 152 may not be affected.

In the graphic representation 170C, the object 158 is moved to the right along the arch form. Now that the object 152 is anchored to a fixed status, the in-between objects 154, 156 both resize (e.g., enlarge) in the same amount to a bigger size than the old ones' 154o, 156o to make up the distance caused by the moving of the object 158. As a result, the objects 152, 154, 156, 158 in the arch form are still packed to each other.

In the depicted embodiment of the graphic representation 170D, the object 154 is moved to the right along the arch form. The other objects 156, 158 both move to the right along with the moving object 154 to keep packing to their neighboring objects. In order to keep the object 152 to still pack to the moving neighbor object 154, the anchoring of the object 152 to the fixed position is broken and the object 152 is moved with the object 154 to pack to it. The fixed position of the object 152 may be lost. In other embodiments, the anchoring of the object 152 to the fixed status may not be broken, and the object 152 may stay anchored to the fixed status. As a result, in such embodiments, the arch form may be broken and the object 152 may be disconnected from the rest objects of the arch form.

Referring now to FIG. 1E, depicted are graphic representations 180A-180C showing mesial packing with both end objects anchored according to one embodiment. As depicted in dark, the both end objects 152, 158 of the arch form are anchored. In the graphic representation 180A, the anchored objects 152, 158 and the in-between objects 154, 156 compose the arch form. In the graphic representation 180B, the object 156 is moved to the upper right off the arch form, as indicated by the depicted arrow on it. The object 154 is, responsively, resized (e.g., enlarged) to make up the distance created by the moving of the object 156. The object 154 is changed to a bigger sized than the old one's 154o. All the objects 152, 154, 156, 158 are still packed to one another after the changes.

In the depicted embodiment of the graphic representation 180C, the object 154 is firstly enlarged (e.g., to respond to a user's action such as click and drag) to a bigger size than the old one's 154o. Now that the space (or distance) between the two anchored objects 152, 158 are fixed, the object 156 may be shrunk to make room for the enlarged object 154. Therefore, due to the enlargement of the object 154, the object 156 is resized to a smaller sized than the old one's 156o, to keep all objects 152, 154, 156, and 158 packing to one another in the arch form.

Figure 1F:
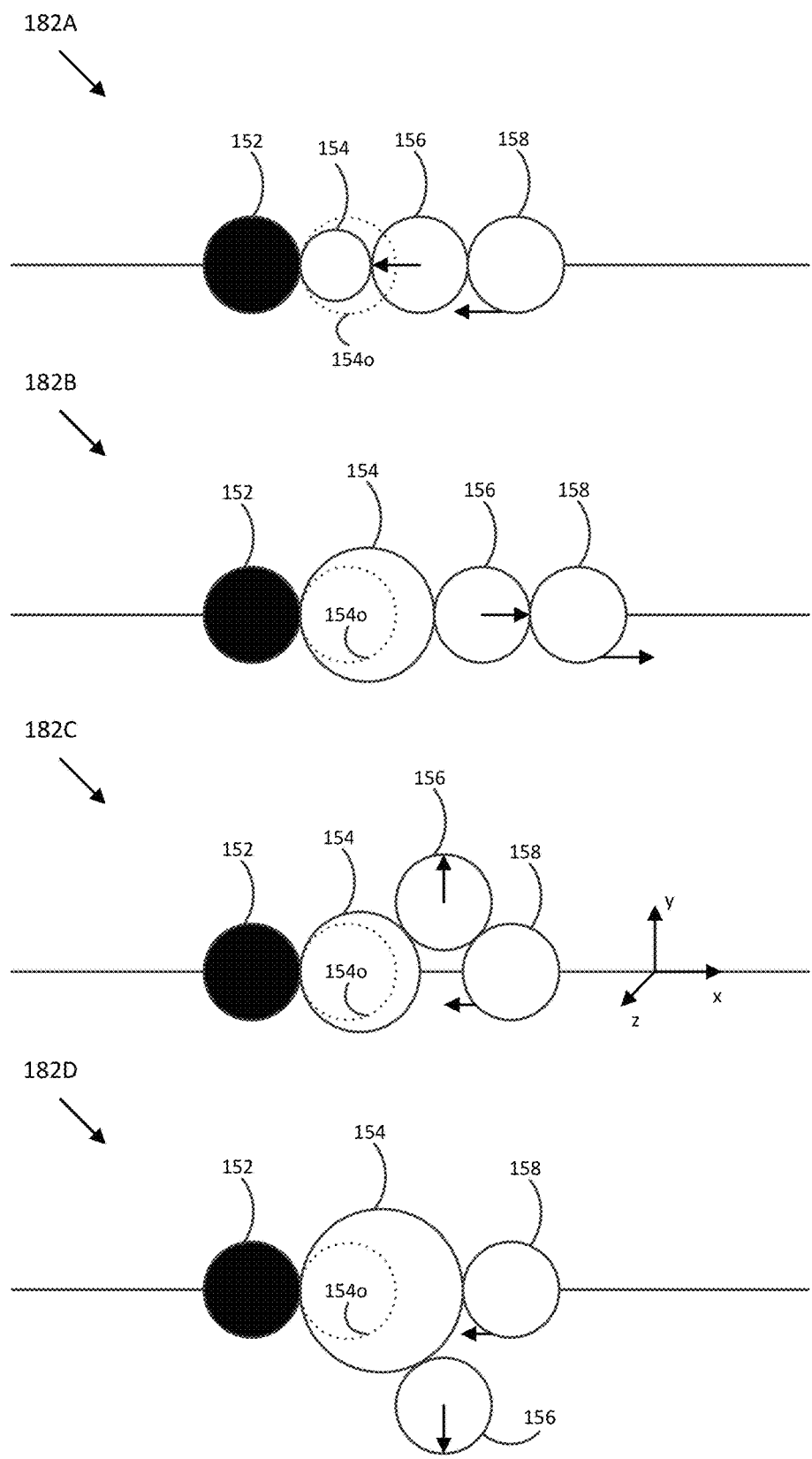
FIG. 1F is graphic representations showing mesial packing with both end objects anchored according to another embodiment.

Referring now to FIG. 1F, depicted are graphic representations 182A-182D showing mesial packing with both end objects anchored according to another embodiment. In the depicted embodiment of the graphic representation 182A, the object 156 is moved to left along the arch form. For example, responsive to a user's dragging the object 156 to left along the arch form, the software moves the object 156 to left along the arch form. The object 154 is thus squeezed since the adjacent object 152 on the other side is anchored. The object 154 is scaled to a smaller size than the old one's 154o to make room for the coming object 156. The object 158 was previously anchored to a fixed position. Responsive to the moving of the object 156, the object 158 is moved to the left to pack to the object 156. Therefore, the anchoring of the object 158 is broken. In another embodiment, the anchoring of the object 158 may not be broken and the object 158 may still be in the fixed status. However, the packing between the object 156 and 158 may be broken.

In the depicted embodiment of the graphic representation 182B, the object 156 is moved to right along the arch form. The neighboring object 154 is enlarged to a bigger size than the old one's 154o to take the space or distance created by the moving object 156, while packing to the object 156. The object 154 packs to the anchored object 152 on the other side. Being pushed by the moving object 156, the anchored object 158 is moved to right along the arch form while packing to the object 156. As a result, the anchoring of the object 158 is broken. Similarly, in another embodiment, the anchoring of the object 158 may not be broken and the object 158 may still be in the fixed status. However, the packing between the object 156 and 158 may be broken.

In the depicted embodiment of the graphic representation 182C, the object 156 is moved straight up away from the arch form. That is, the object 156 is moved along the y-axis of the Cartesian coordinate system. Thus, there is some space created by the moving of the object 156. The neighboring object 154 is resized to a larger one than the old one 154o to make up the space and thus keep packing to the moving object 156. On the other side of the object 154, it keeps packing to the anchored object 152. On the other side of the object 156, the anchored object 158 is moved to left to make up the space created by the up-straight moving of the object 156 and thus still keeps packing to the object 156. In such an embodiment, the contact distance between the objects 156, 158 may be calculated as the space distance between them. After the moving of the object 156, the space distance between the objects 156, 158 is not zero, and therefore the anchored object 158 is moved to pack to the up-moving object 156. As a result, the anchoring of the object 158 is broken. The fixed status of the object 158 is lost.

In another embodiment, the anchored object 158 may stay at the fixed anchoring status because the contact distance along the arch form (x-axis) between the object 156 and the object 158 does not change. For example, the contact distance between the objects may be calculated along any axis of the coordinate system, such as along x-axis, y-axis and z-axis of the Cartesian coordinate system. Along the x-axis (the arch form), the closest point to point distance between the object 156 and the object 158 is still zero even when the object 158 is not moved. Therefore, the anchored object 158 stays anchored. In yet other embodiments, the contact distance between objects along one or more other axes, or calculated in one or more other ways may be considered to determine if the objects still pack to each other.

Similarly, in the depicted embodiment of the graphic representation 182D, the object 156 is moved straight down from the arch form. The object 154 is enlarged to a bigger size than the old one's 154o. The anchored object 158 is moved to the left to make up the distance generated by the moving of the object 156. When the object 156 is moved far enough and to be completely off the arch form, the object 154 and the object 158 may pack to each other rather than both pack to the object 156.

Figure 1G:
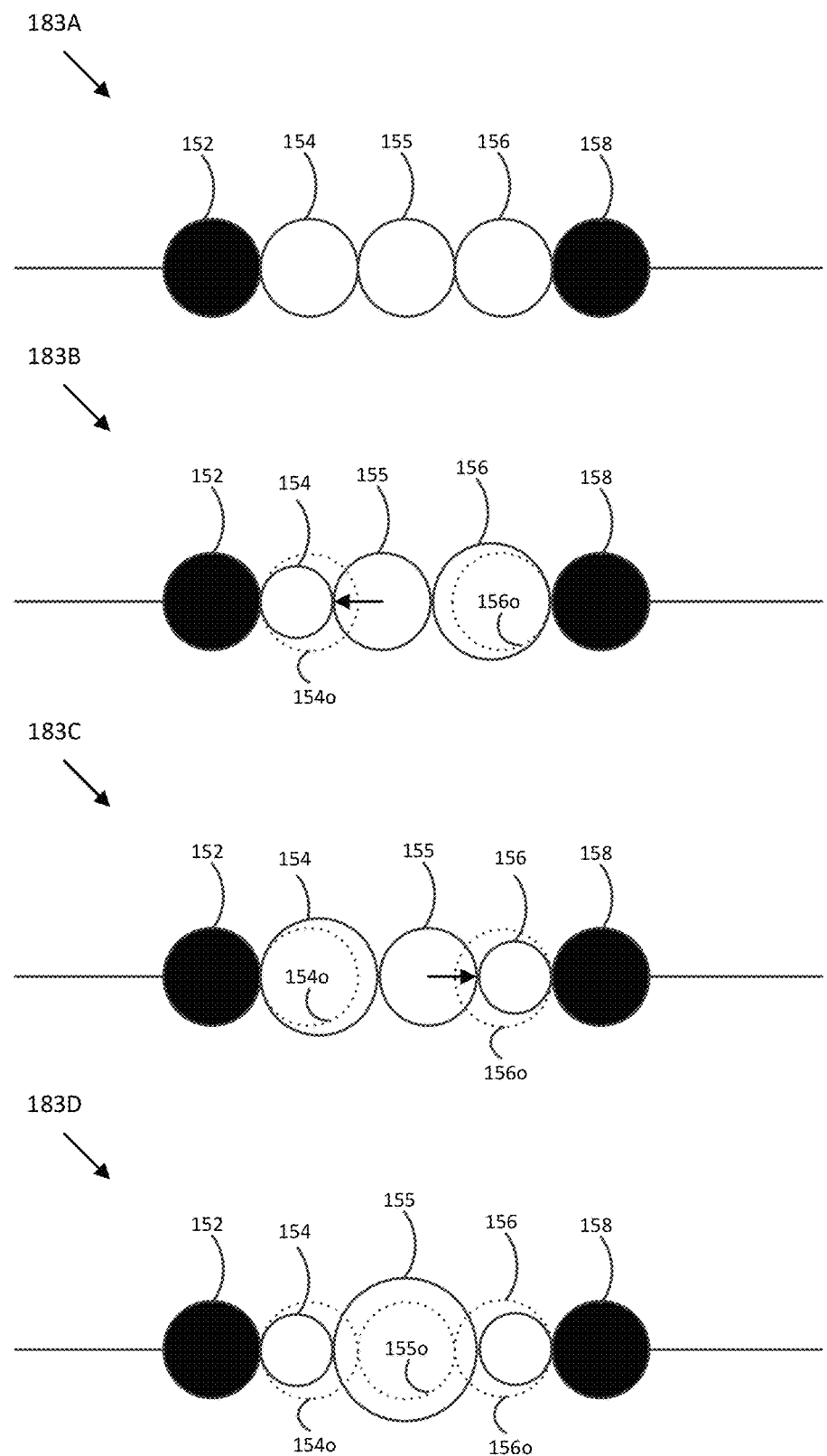
FIG. 1G is graphic representations showing mesial packing with both end objects anchored according to yet another embodiment.

Referring now to FIG. 1G, depicted are graphic representations 183A-183D showing mesial packing with both end objects anchored according to yet another embodiment. In the depicted embodiment of the graphic representation 183A, objects 152, 154, 155, 156, 158 compose an arch form. The objects 152 and 158 are snapped or anchored at either end of the arch form. The objects 154, 155 and 156 are in-between the anchored objects 152 and 158. In the depicted embodiment of the graphic representation 183B, the object 155 is moved to left along the arch form and therefore squeezes the neighboring object 154 on its left. Since the object 152 is anchored, the adjacent object 154 cannot move without breaking the packing Thus the object 154 is scaled to a smaller size than the old one's 154o to make room for the pushing object 155. On the other side of the object 155, there is more space left after the moving of the object 155. Thus the object 156 is scaled to a larger size than the old one's 156o to occupy the space and to keep packing to the moving object 155, while also keeping packing to the anchored object 158 on the other side.

Similarly, in the depicted embodiment of the graphic representation 183C, the object 155 is moved to right along the arch form, and therefore is pushing into the object 156 and creating space between itself and the object 154. Thus, the object 156 is resized to a smaller one than the old one 156o; the object 154 is resized to a larger one than the old one 154o. The objects 152, 154, 155, 156, 158 still keep packing to their neighboring objects respectively.

In the depicted embodiment of the graphic representation 183D, the object 155 is scaled to a bigger size than that of the old one 155o, and therefore is pushing into both the neighboring objects 154 and 156. The objects 154 and 156 are both resized to a smaller one 154o, 156o, respectively, in the same amount to accommodate the enlarged object 155, without breaking the anchoring of the objects 152 and 158. The objects 152, 154, 155, 156, 158 still keep packing to their neighboring objects respectively during and/or after the changes.

In one embodiment, the contour or shape of an object may not be symmetric in all three dimensions ("3D"). Therefore, the orientation of an object matters in some situations. For example, rotation of the asymmetric object in some dimension may cause the asymmetric object push into one or more of its neighboring objects. Due to the mesial packing, the neighboring objects may perform collision, and move or resize to keep packing to the rotated object. Such scenarios are described in detail with reference to FIGS. 1H, 1K and 1L.

Figure 1H:
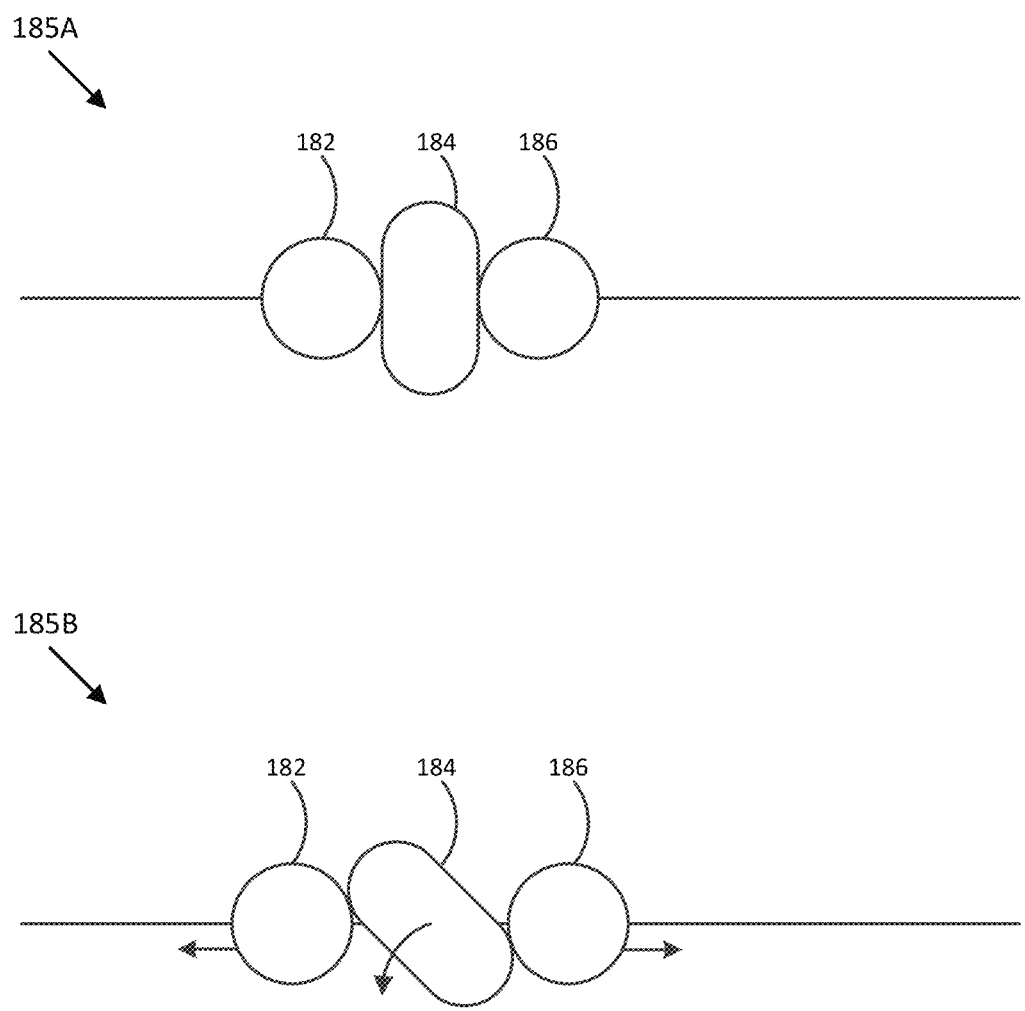
FIG. 1H is graphic representations showing mesial packing responsive to rotation of an object according to one embodiment.

Referring now to FIG. 1H, depicted are graphic representations 185A, 185B showing mesial packing responsive to rotation of an object according to one embodiment. Elements 182, 184, 186 are graphic representations of objects composing an arch form. The objects 182, 184, 186 can include, but not be limited to, a tooth crown, a tooth in a bridge, a tooth for implant, partial denture, etc. In the depicted graphic representations 185A and 185B, the objects 182, 184, 186 compose an arch form, without any object anchored. The object 184 is rotated clockwise in the depicted plane. Due to its asymmetric contour, the rotating object 184 pushes into the neighboring objects 182, 186. The objects 182, 186, therefore, perform collision and move away from the rotating object 184 to make room for it. As a result, the objects 182, 184, 186 in the arch form are still packed to one another.

Figure 1K:
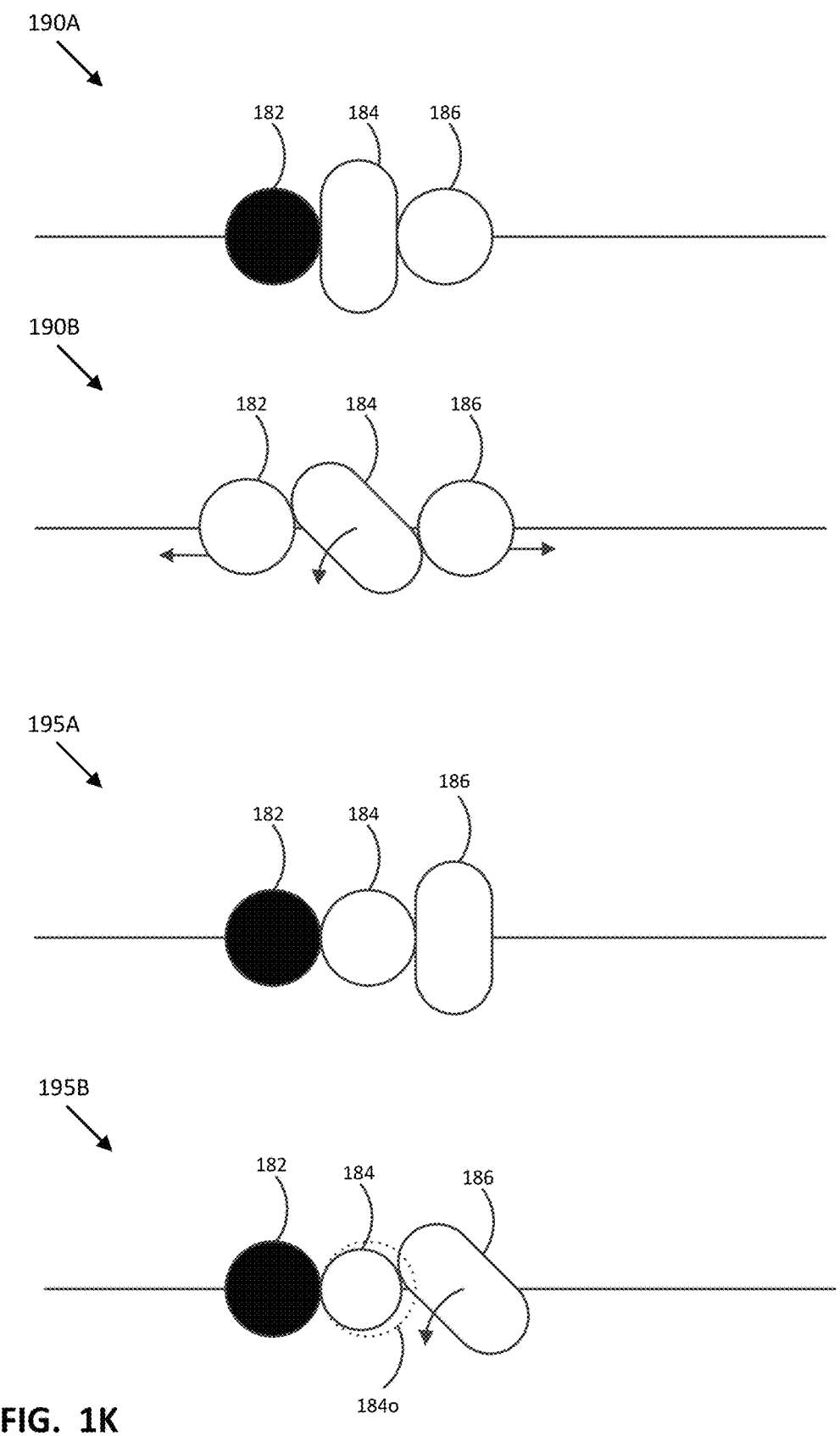
FIG. 1K is graphic representations showing mesial packing with one end object anchored responsive to rotation of anon-anchored object according to one embodiment.

Referring to FIG. 1K, depicted are graphic representations 190A, 190B, 195A, 195B showing mesial packing with one end object anchored responsive to rotation of a non-anchored object according to one embodiment. Similar to FIG. 1H, elements 182, 184, 186 are graphic representations of objects composing an arch form. The objects 182, 184, 186 can include, but not be limited to, a tooth crown, a tooth in a bridge, a tooth for implant, partial denture, etc. In the depicted graphic representation 190A, the end object 182 is snapped or anchored to a fixed status (e.g., position, size, orientation, shape, etc.), as shown in dark. The object 184 has an asymmetric shape (or contour). In the depicted embodiment of the graphic representation 190B, the object 184 is rotated clockwise in the depicted plane. Due to its asymmetric contour, the rotating object 184 pushes into the non-anchored neighboring object 186 along the arch form. The object 186, therefore, performs collision and moves to right along the arch form and away from the rotating object 184 to make room for it. Moreover, the rotating object 184 is also pushing into the anchored object 182. As a result, the anchored object 182 is moved to left along the arch form to accommodate the rotating object 184. The anchoring of the object 182 is thus broken. The objects 182, 184, 186 in the arch form are still packed to their neighboring objects respectively during and/or after the changes. In another embodiment, the anchoring object 182 may still stay in the fixed status and the anchoring may not be broken. For example, the object 184 may be moved to right while being rotated.

In the graphic representation 195A, the object 186 has an asymmetric shape (or contour). The objects 182, 184, 186 pack to each other, and object 182 is anchored. When the asymmetric object 186 rotates, as depicted by the graphic representation 195B, its neighboring object 184 is pushed and resized (e.g., shrunk) to a smaller size than the old one's 184o to make room for the rotating object 186. The object 184 still packs to the rotating object 186 on one side, and packs to the anchored object 182 on the other side.

Figure 1L:
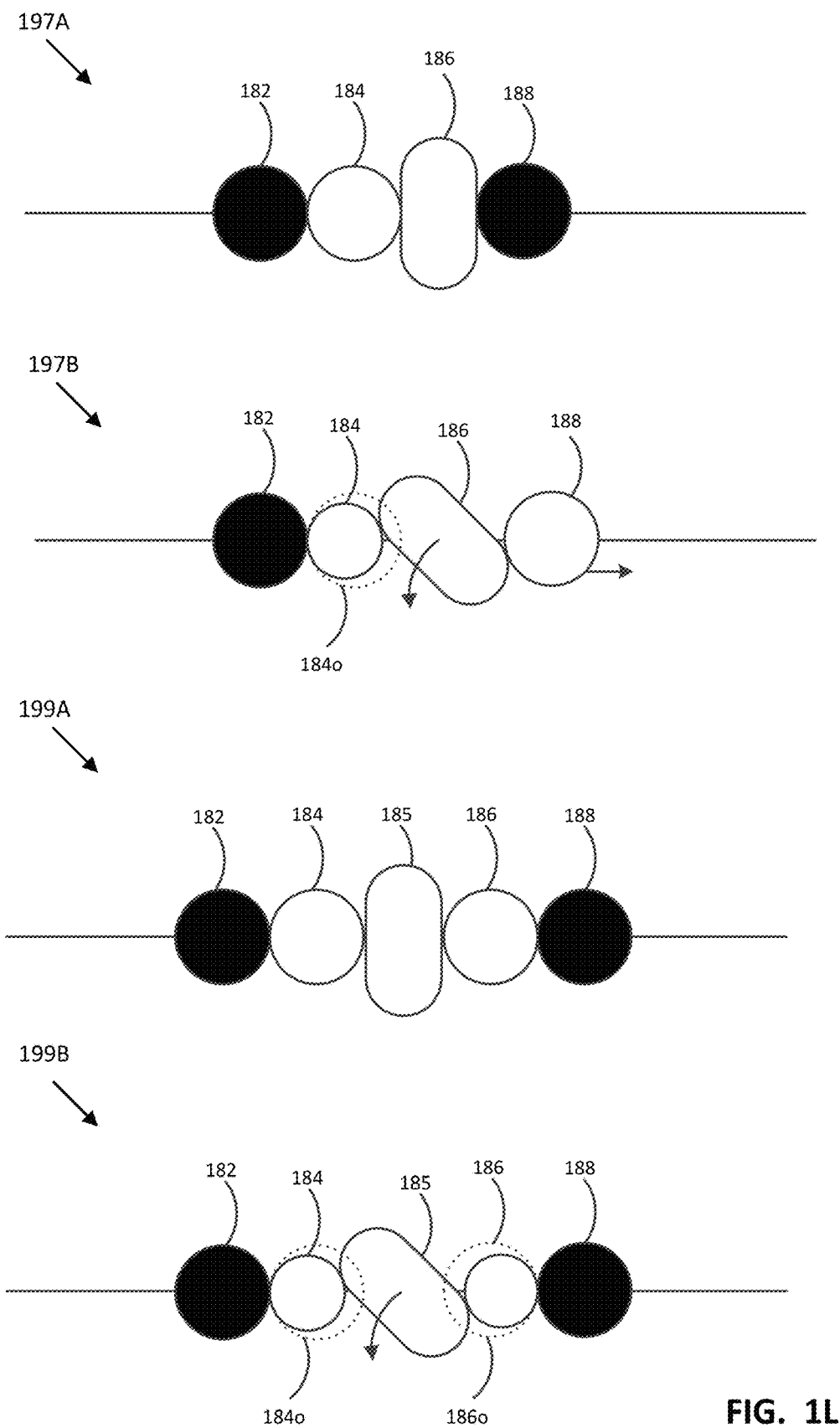
FIG. 1L is graphic representations showing mesial packing with both end objects anchored responsive to rotation of a non-anchored object according to one embodiment.

Referring now to FIG. 1L, depicted are graphic representations 197A, 197B 199A and 199B showing mesial packing with both end objects anchored responsive to rotation of a non-anchored object according to one embodiment. In the depicted embodiments of the graphic representations 197A-197B, an arch form includes objects 182, 184, 186, 188. Both end objects 182, 188 are anchored to a fixed status, and are shown in dark. The object 186 has an asymmetric shape (or contour).

When the object 186 rotates, as depicted in graphic representation 197B, it pushes into the non-anchored neighboring object 184. Since the object 184 packs to the anchored object 182 on the other side and cannot move, the object 184 is therefore resized to a smaller size than the old one's 184o to accommodate the rotating object 186. On the other side of the rotating object 186, the rotating object 186 is also pushing into the anchored object 188. The object 188 is therefore moved to right along the arch form to make room for the rotating object 186. The fixed status of the object 188 is thus lost. All the objects 182, 184, 186, 188 in the arch form still keep packing to their neighboring objects respectively during and/or after the rotation of the object 186. In another embodiment, the object 188 may stay in the fixed status and the anchoring may not be lost. For example, the object 186 may be scaled to a smaller size while being rotated.

In the depicted embodiment of the graphic representations 199A and 199B, an arch form includes objects 182, 184, 185, 186, 188. Both end objects 182, 188 are anchored to a fixed status, and are shown in dark. The object 185 has an asymmetric shape (or contour). When the object 185 rotates, as depicted in graphic representation 199B, it pushes into both of the non-anchored neighboring object 184 and the non-anchored neighboring object 186. As a result, the objects 184 and 186 are both scaled to a smaller size than those of the old ones 184o, 186o, respectively, to make room for the rotating object 185. For example, the object 184 and 186 may shrink in the same amount. The objects 182, 184, 185, 186, 188 in the arch form still keep packing to their neighboring objects respectively during and after the rotation of the object 185. In addition, the anchoring of the objects 182 and 188 are retained.

In one embodiment, the change of an object in shape or contour may cause one or more of its neighboring objects to move or resize to keep packing to the shape-changed object. For example, the object may be changed in its shape or replaced by a new object with a different shape so that the distance between it or the new object and one of the adjacent objects becomes larger than a pre-defined limit. Therefore, the adjacent object may be moved or resized to make up the distance to keep packing to the shape-changed object. Those of skill in the art may also appreciate other embodiments in which a change of an object in shape may lead to one or more parametric changes of its neighboring objects.

Figure 2A:
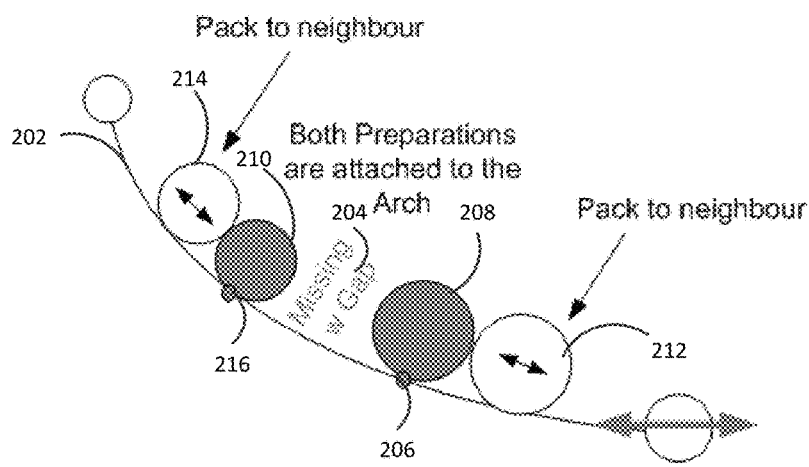
FIGS. 2A-2B are graphic representations showing mesial packing according to another embodiment.
Figure 2B:
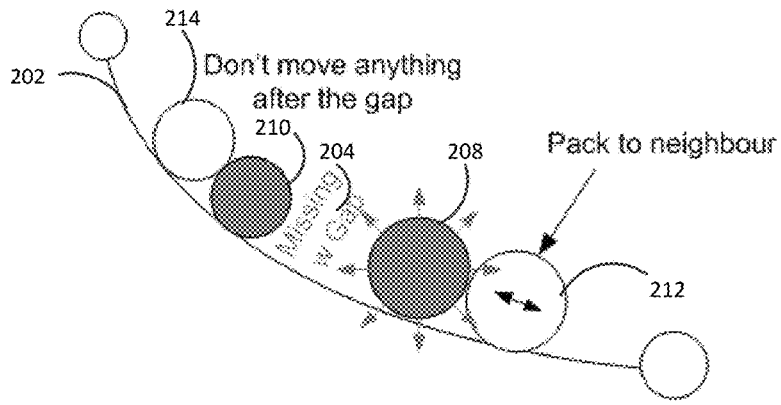

Referring now to FIGS. 2A-2B, mesial packing in arch motion and manual scaling of tooth are depicted according to another embodiment. Referring to FIG. 2A, a graphic representation 200 shows mesial packing of teeth having a missing tooth with a gap in arch motion according to one embodiment. Element 202 is a graphic representation of an arch. Elements 208, 210 are graphic representations of two preparation teeth that are attached to the arch 202 at invisible attachment points 206, 216, respectively. Element 204 is a graphic representation of a gap between the two preparation teeth 208, 210. The gap 204 represents a missing tooth with a gap. The teeth 208, 210 both pack to the gap 204. In other words, the teeth 208, 210 pack to each other by staying within a certain distance to each other. The certain distance can be the size or width of the gap 204, which is pre-determined by a user or administrator of the dental restoration design system. Elements 212, 214 are graphic representations of neighboring teeth to the preparation teeth 208, 210.

In the embodiment where none of the teeth 212, 208, 210, 214 are anchored, the teeth 212, 214 can move in both directions along the arch 202, as depicted by the double arrows on the teeth, to pack to the preparation teeth 208, 210, respectively, when either of the teeth 208, 210 is moved or resized. For example, when the preparation tooth 208 is moved or resized along the arch 202, its neighbor tooth 212 moves accordingly to keep packing to the preparation tooth 208, such as with zero contact distance to the preparation tooth 208. In addition, the tooth 210 is moved or resized to keep packing to the tooth 208 with a gap 204 and the tooth 214 moves to the neighbor tooth 210. In other embodiments, all teeth 208, 210, 212, 214 can move or resize to pack to one another when any one of these teeth is moved or resized by a user. For example, when the tooth 212 is moved, the tooth 208 moves or resizes to pack to the moving tooth 212. Additionally, the tooth 210 also moves or resizes to pack to the tooth 208 with a gap 204, and the tooth 214 also moves or resizes to pack to the tooth 210.

Referring to FIG. 2B, a graphic representation 230 shows mesial packing of teeth having a missing tooth with a gap in scaling of tooth according to one embodiment. In the depicted embodiment, the tooth 208 is resized (e.g., scaled to a larger size) and therefore is pushed into its neighboring tooth 212. Thus, the tooth 212 performs collision and move along the arch 202 to stay within zero contact distance to the resized tooth 208. In one embodiment, the tooth 212 may also perform rotation along the arch 202 to keep contact with the resized tooth 208. In the one embodiment, the teeth 210, 214 on the other side of the gap 204 do not move, but stay in their original positions respectively. As described above, the packing of the preparation teeth 208, 210 to the gap 204 may also be interpreted as the preparation teeth 208, 210 keep packing with a certain distance (e.g., larger than zero) pre-defined by a user or administrator of the design program. Therefore, by resizing the tooth 208, the distance or gap between it and the tooth 210 may become smaller or larger. In other embodiments, the teeth 210, 214 may also move or resize to pack to the resized tooth 208 with a gap 204.

In one embodiment, similar to those described in FIGS. 1A-1B, these teeth 212, 208, 210, 214 can be virtual library teeth forming the arch form 202. These teeth have similar behaviors to those described in FIGS. 1A-1B when one end tooth or both end teeth is snapped or anchored. For example, if the tooth 212 is anchored, when the tooth 214 is moved to left along the arch 202, the tooth 210 moves or expands in size to pack to the moving tooth 214. In one embodiment, the tooth 208 expands in size to pack to the tooth 210 with a gap and pack to the anchored tooth 212. In some embodiments, either one of the teeth 208, 210 between the anchored tooth 212 and the moving tooth 214 may change significantly enough so that the other in-between tooth does not have to change in position or size to keep all teeth in the arch form 202 packing to one another. If both teeth 212, 214 are anchored, one of the teeth 208, 210 between the two anchored teeth 212, 214 may resize to keep all teeth packing to their neighboring teeth when any other of the teeth 208, 210 is resized. Other embodiments of how the arch form (or teeth) behaves where one or both ends are anchored and one of the other teeth is moved or resized may also be recognized by those of skill in the art.

Figure 2C:
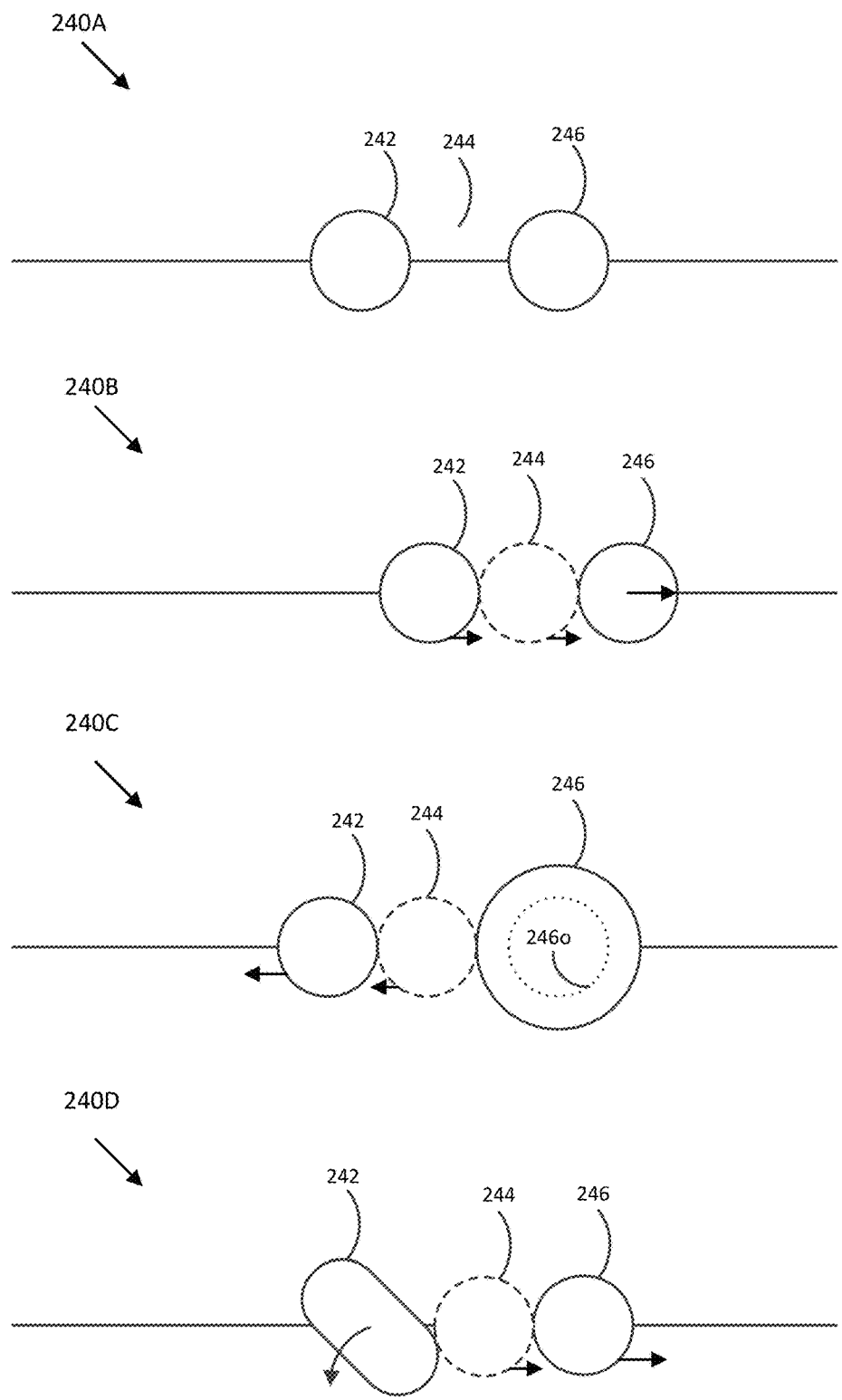
FIG. 2C is graphic representations showing mesial packing of an arch form having a missing object with gap and no object anchored according to one embodiment.

The missing tooth with gap 204 can be treated as an invisible tooth. The mesial packing behaviors of the objects are described in further detail and in many embodiments with reference to FIGS. 2C-2E. Referring now to FIG. 2C, depicted are graphic representations 240A-240D showing mesial packing of an arch form having a missing object with gap and no object anchored according to one embodiment. In the depicted embodiment of 240A, an arch form has two objects 242, 246 and a missing object with a gap 244. Both objects 242, 246 packs to the missing object with the gap 244. In the graphic representation 240B, the object 246 is moved to right along the arch form. The missing object with the gap 244 and the object 242 also move with it to right along the arch form to keep packing to each other. As a result, the objects 242, 246 both still keep packing to the missing object with the gap 244.

In the graphic representation 240C, the object 246 is resized (e.g., enlarged) to a bigger size than the old one's 246o, and therefore pushes into the neighboring missing object with the gap 244. As a result, the missing object with the gap 244 and the other object 242 both move to left to make room for the enlarged object 246. The moving objects 242 and the enlarged object 246 both keep packing to the missing object with the gap 244.

In the graphic representation 240D, element 242 is a graphic representation of an asymmetric object. When the object 242 rotates, it pushes into the missing object with the gap 244. The missing object with the gap 244 and the object 246 packing to it both move to the right to accommodate the rotating object 242.

Figure 2D:
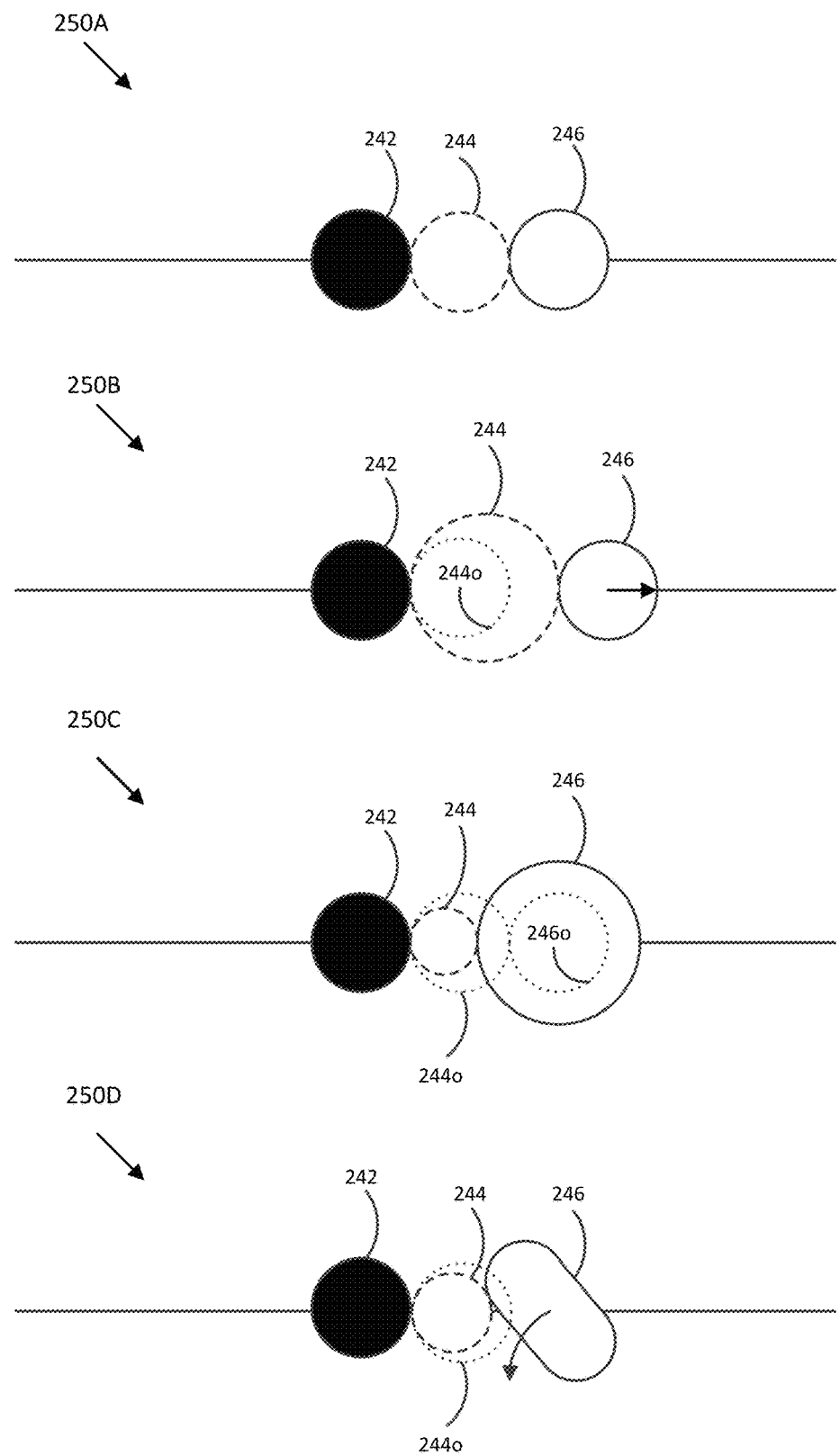
FIG. 2D is graphic representations showing mesial packing of an arch form having a missing object with gap and one end object anchored according to one embodiment.

Referring now to FIG. 2D, depicted are graphic representations 250A-250D showing mesial packing of an arch form having a missing object with gap and one end object anchored according to one embodiment. Similar to the embodiment of FIG. 2C, an arch form has two objects 242, 246 and a missing object with a gap 244. Both objects 242, 246 pack to the missing object with the gap 244. In the depicted embodiment of FIG. 2D, one end object 242 is snapped or anchored to a fixed status (e.g., position, size, posture, etc.). In the graphic representation 250A, the missing object with the gap 244 is shown in a dotted line.

In the graphic representation 250B, the other end object 246 moves to the right along the arch form. Since the end object 242 is anchored to the fixed position and cannot move, in order to keep packing to the end object 242, the missing object with the gap 244 also cannot move. Therefore, the in-between missing object with the gap 244 is resized (e.g., enlarged) to a bigger size than the old one's 244o to make up the distance or space created by the moving of the other end object 246. Both objects 242, 246 still keep packing to the missing object with the gap 244.

In the graphic representation 250C, the other end object 246 is resized (e.g., enlarged) to a bigger size than the old one's 246o. For example, the object 246 is enlarged concentrically. Now that the end object 242 is anchored, the missing object with the gap 244 is resized (e.g., shrunk) to a smaller size than the old one's 244o to make room for the enlarged end object 246. As a result, both objects 242, 246 still keep packing to the missing object with the gap 244.

In the graphic representation 250D, the other end object 246 has an asymmetric contour. When the other end object 246 is rotated clockwise on the plane depicted, it pushes into the missing object with the gap 244. Given that the end object 242 to which the missing object with the gap 244 packs is anchored, the missing object with the gap 244 is, therefore, resized (e.g., shrunk) to a smaller size than the old one's 244o to make room for the rotated object 246. As a result, both objects 242, 246 still keep packing to the missing object with the gap 244.

Figure 2E:
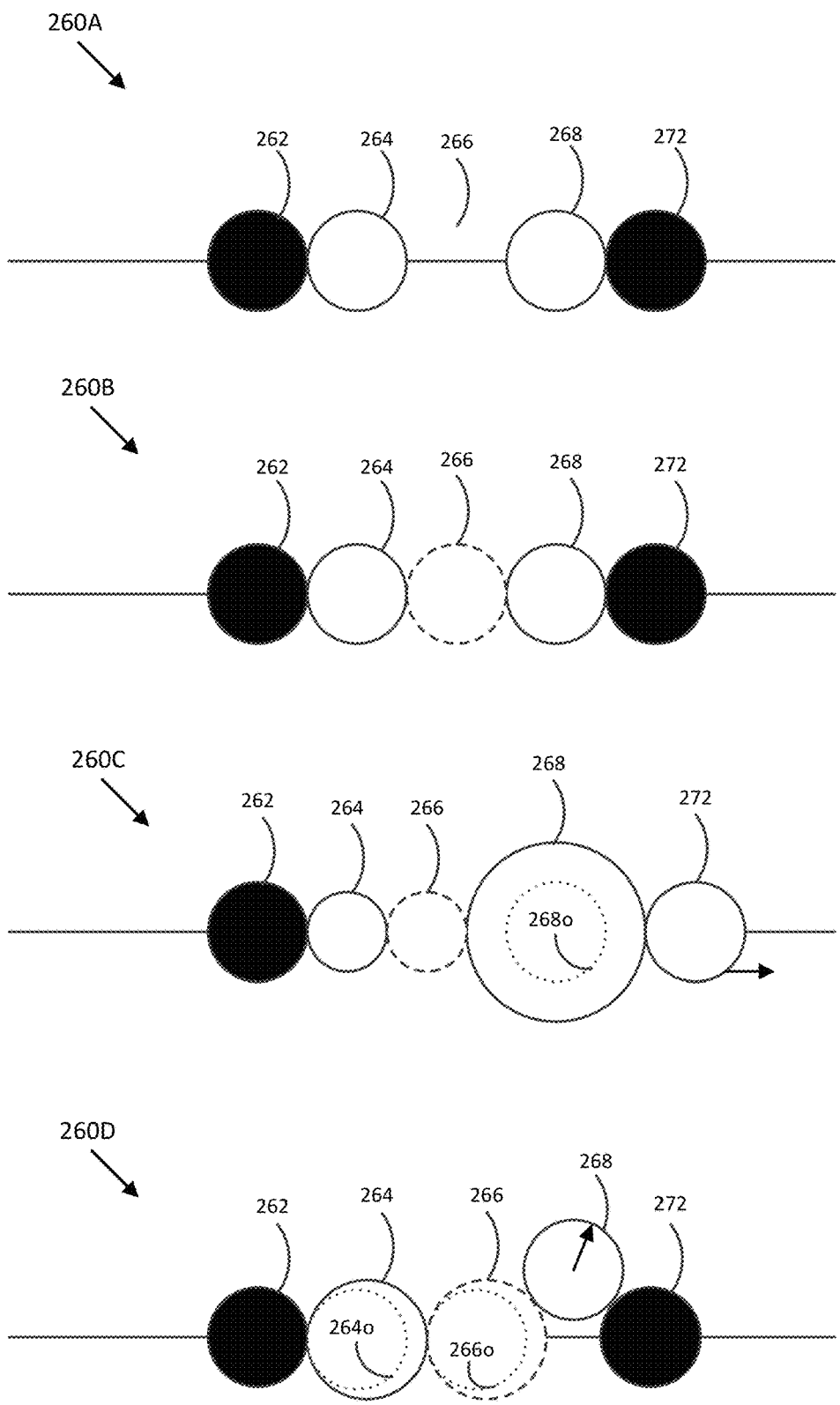
FIG. 2E is graphic representations showing mesial packing of an arch form having a missing object with gap and both end objects anchored according to one embodiment.

Referring to FIG. 2E, depicted are graphic representations 260A-260D showing mesial packing of an arch form having a missing object with gap and both end objects anchored according to one embodiment. Elements 262, 264, 268, 272 are graphic representations of objects composing an arch form. The objects 262, 264, 266, 268, 272 can include, but not be limited to, a tooth crown, a tooth in a bridge, a tooth for implant, partial denture, etc. Both end objects 262, 272 are snapped or anchored to a fixed status (e.g., position, size, posture, etc.), as shown in dark. The element 266 is a graphic representation of a missing object with a gap. In the graphic representation 260B, the missing object 266 with a gap is depicted in dashed lines.

In the graphic representation 260C, the object 268 is enlarged to a bigger size than the old one's 268o. For example, the object 268 is enlarged concentrically. Accordingly, the objects 264, 266 are resized in the same amount to a smaller size to make room for the enlarged object 268, given that the object 262 is anchored to the fixed position and size. On the other side of the enlarged object 268, the object 272 is moved to right along the arch from to make room for the enlarged object 268. Therefore, the anchoring of the object 272 is broken. The fixed status of the object 272 is lost. In another embodiment, the object 272 may stay in the fixed status and the anchoring of it may not be broken. For example, the object 268 may expand to the left side.

In the graphic representation 260D, the object 268 is moved upper right from the arch form. As a result, the objects 264, 266 are both resized in the same amount to a larger size to make up the distance caused by the moving of the object 268, to keep all objects in the arch form to pack together. As depicted, the missing object with a gap 266 behaves just like an invisible object, performing the same changes as other objects in the arch form.

Figure 2F:
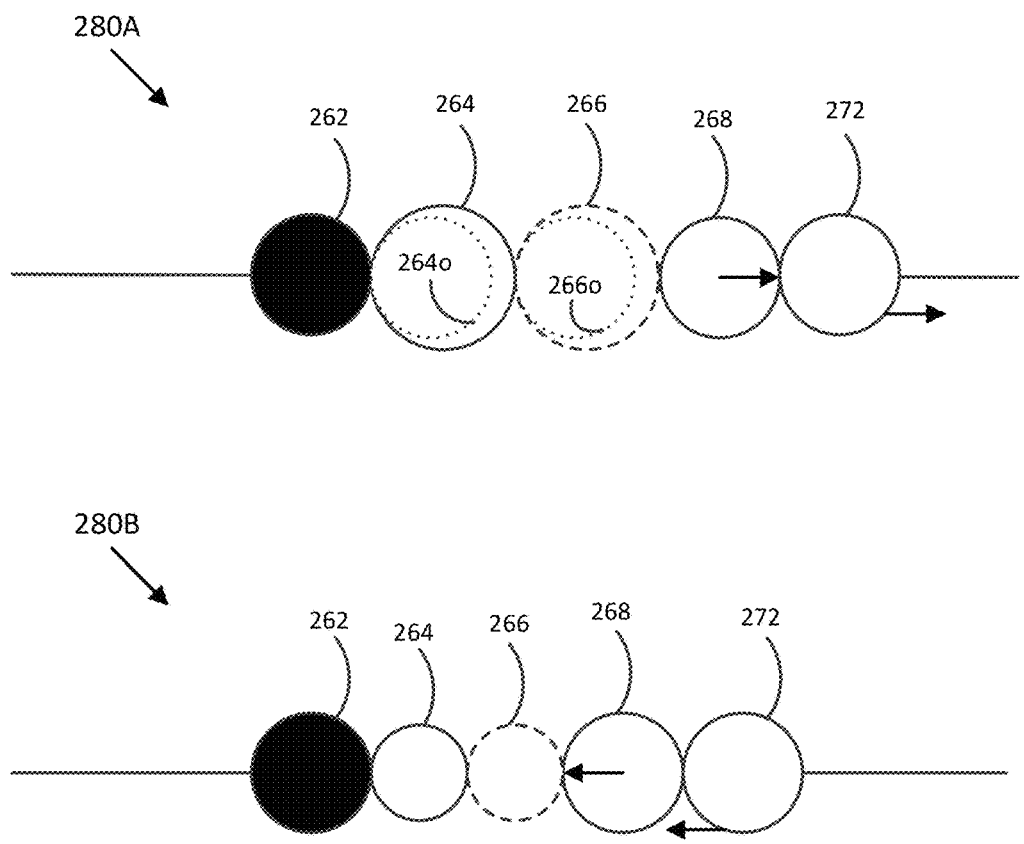
FIG. 2F is graphic representations showing mesial packing of an arch form having a missing object with gap and both end objects anchored according to another embodiment.

Referring to FIG. 2F, depicted graphic representations 280A-280B showing mesial packing of an arch form having a missing object with gap and both end objects anchored according to another embodiment. Similar to FIG. 2E, elements 262, 264, 268, 272 are graphic representations of objects composing an arch form. The objects 262, 264, 266, 268, 272 can include, but not be limited to, a tooth crown, a tooth in a bridge, a tooth for implant, partial denture, etc. Both end objects 262, 272 are snapped or anchored to a fixed status (e.g., position, size, orientation, shape, or any combination thereof), as shown in dark. The element 266 is a graphic representation of a missing object with a gap. In the graphic representations 280A-280B, the missing object 266 with a gap is depicted in dashed lines.

In the graphic representation 280A, the object 268 is moved to right along the arch form. As a result, the objects 264, 266 are both resized in the same amount to a larger size to make up the distance caused by the moving of the object 268, to keep packing to their neighboring objects respectively. The missing object with a gap 266 behaves just like an invisible object, performing the same changes as other objects in the arch form. On the other side of the moving object 268, the anchored object 272 is pushed by the object 268 and is moved to the right along the arch form too. Therefore, the anchoring of the object 272 is broken. The object 272 keeps packing to the object 268, and loses the fixed status (e.g., position, orientation, size, shape, or any combination thereof). In another embodiment, the object 272 may stay in the fixed status and the anchoring of it may not be broken. For example, the object 268 may be scaled to a smaller size while being moved.

In the graphic representation 280B, the object 268 is moved to left along the arch form. As a result, the objects 264, 266 are both resized in the same amount to a smaller size to accommodate the coming of the object 268, to keep packing to their neighboring objects respectively. On the other side of the moving object 268, the anchored object 272 is moved to left along the arch form to keep packing to the moving object 268. Accordingly, the anchoring of the object 272 is broken and the object 272 loses the fixed status. In another embodiment, the object 272 may stay in the fixed status and the anchoring of it may not be broken. For example, the object 268 may be scaled to a larger size while being moved.

Exemplary Graphical User Interfaces

Figure 3A:
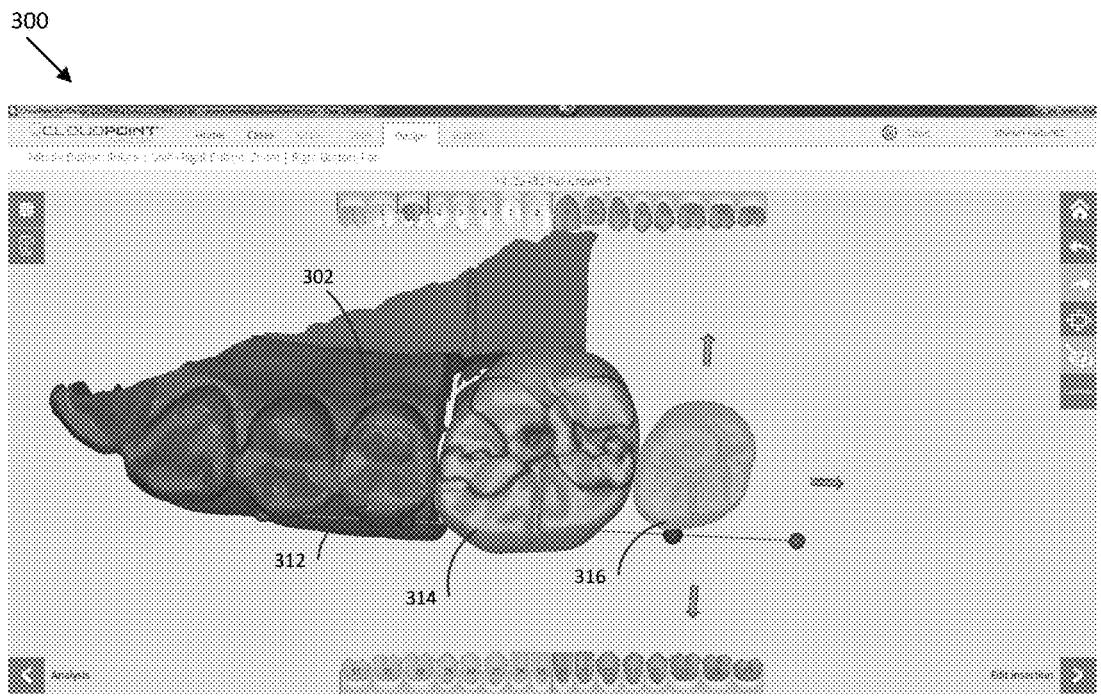
FIGS. 3A-3B are graphic representations of mesial packing effect in single crown design provided by a dental restoration design program according to one embodiment.
Figure 3B:
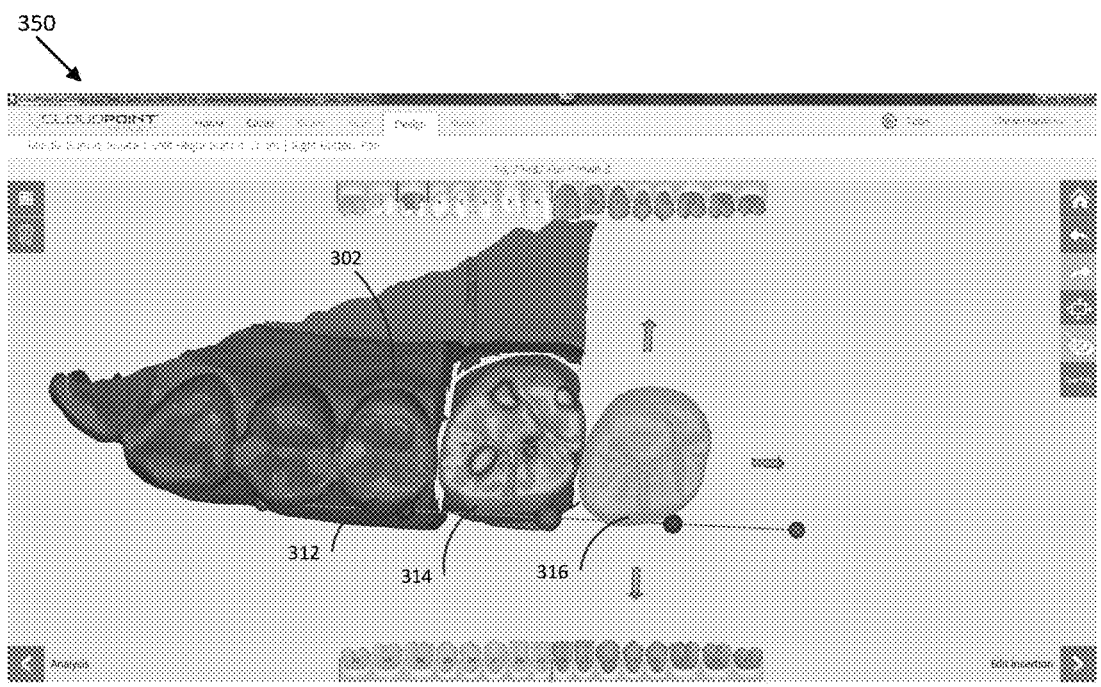

Referring now to FIGS. 3A-3B, mesial packing effect in single crown design provided by a dental restoration design program is depicted according to one embodiment. Referring to FIG. 3A, a user interface 300 is provided by a dental restoration design program to a user. The user interface 300 includes a graphic representation of scanned dentition data 302. The user interface 300 also provides a proposed library arch form of teeth, as represented by graphic elements 312, 314, 316 (referred to as library teeth 312, 314, 316). The library teeth 312, 314, 316 are packed to one another and form the arch form. In one embodiment, the tooth 312, 314, or 316 may be a library tooth for a preparation tooth (not shown). In another embodiment, the tooth 312, 314, or 316 may be a library tooth for a non-preparation tooth. In one embodiment, the dental restoration design program provides placement of the arch form of the library teeth 312, 314, 316 to best match the scanned dentition data 302 from the patient's dentition including the preparation tooth. For example, the dental restoration design program snaps the library tooth 312 to the scan data 302. In the depicted FIG. 3A, the library tooth 312 is transparent to indicate that it is snapped to the scan data 302 and thus behaves like an anchor. In one embodiment, the dental restoration design program allows the user to snap the library tooth 312 manually via the user interface 300.

Through the user interface 300, the user can also view and adjust the arch form placement manually using a mouse or any other suitable tools. When the user moves any part of the arch form, the dental restoration design program perform a change of the arch form based upon the mesial packing scheme. For example, as depicted in FIG. 3A, when the user clicks and moves the library tooth 316 to right of the screen (away from the tooth 314), since the library tooth 312 is anchored, the library tooth 314 is the center of the arch form and therefore is scaled (e.g., expands) outward from center point to keep packing to the neighboring teeth 312, 316. Referring to FIG. 3B, when the user moves the library tooth 316 to the left of the screen (pushing into the library tooth 314), since the library tooth 312 is anchored, the library tooth 314 is the center of the arch form and therefore is resized (e.g., shrinks) inward to center point to keep packing to the teeth 312, 316.

Figure 4A:
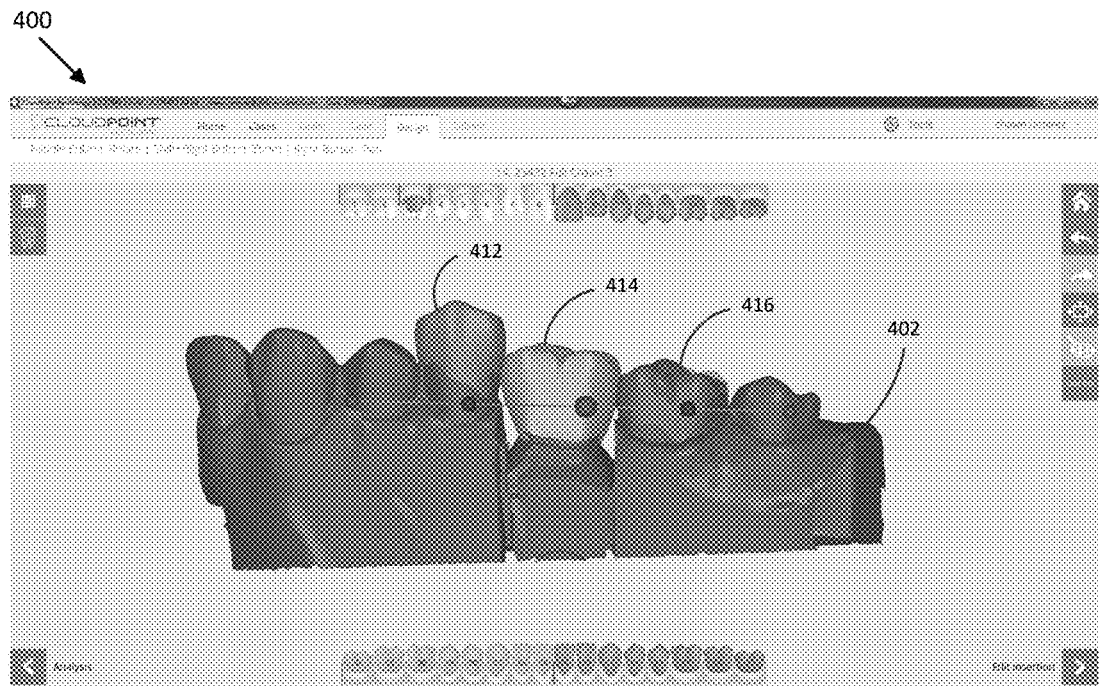
FIGS. 4A-4B are graphic representations of mesial packing during snapping in single crown design provided by a dental restoration design program according to one embodiment.
Figure 4B:
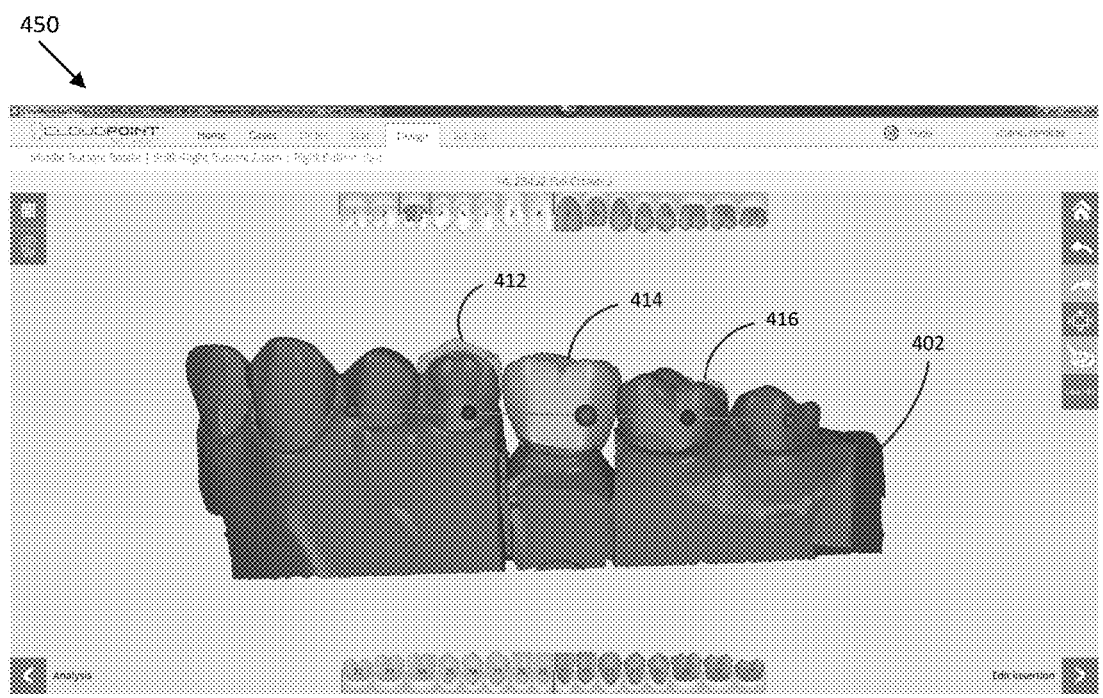

Referring now to FIGS. 4A-4B, mesial packing during snapping in single crown design provided by a dental restoration design program is depicted according to one embodiment. Referring to FIG. 4A, a user interface 400 includes scanned dentition data, as represented by element 402, and an arch form of library teeth, as represented by elements 412, 414, 416. The library teeth 412, 414, 416 are packed to one another and form the arch form. The library tooth 412, 414, 416 may be proposed for any type of tooth in the patient's dentition. The library tooth 416, shown as transparent, is snapped to the scan data 402. The library teeth 412, 414, 416 pack to one another. Referring to FIG. 4B, the user interface 450 shows that the user changes the library tooth 412 and snaps the library tooth 412 to a desired position. Once the library tooth 412 is snapped, it is depicted as transparent. Moreover, in responsive to the changing of the library tooth 412, the library tooth 414 expands outward or shrinks inward to keep packing to its neighboring teeth 412, 416.

Figure 5A:
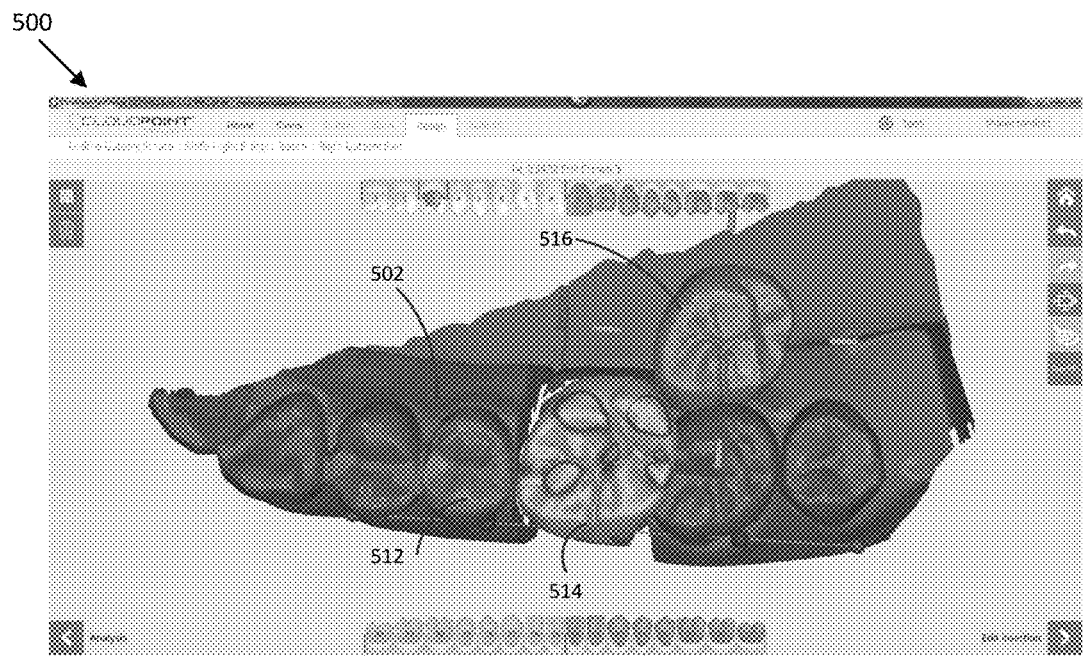
FIGS. 5A-5D are graphic representations of mesial packing during snapping in single crown design provided by a dental restoration design program according to another embodiment.
Figure 5B:
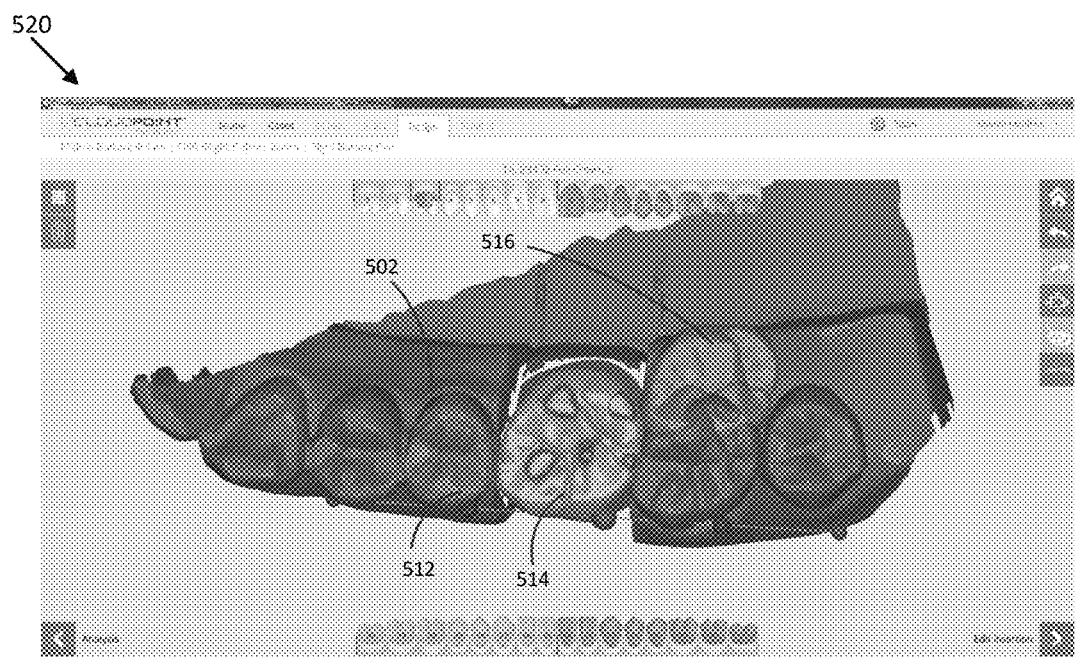

Referring now to FIGS. 5A-5D, mesial packing during snapping in single crown design provided by a dental restoration design program is depicted according to another embodiment. Referring to FIG. 5A, a user interface 500 includes scanned dentition data, as represented by element 502, and an arch form of virtual library teeth, as represented by elements 512, 514, 516. The library teeth 512, 514, 516 are packed to one another and form the arch form. The library tooth 512, 514, 516 may be proposed by the design program for any type of tooth in the patient's dentition, such as a preparation tooth or a non-preparation tooth. The library tooth 512 is snapped to the scan data 502, thus as shown in transparent. When the user moves the other library tooth 516 to snap to corresponding scan data 502, as shown in the user interface 520 in FIG. 5B, the library tooth 514 at the center of the arch form is resized (e.g., shrunk inward) to pack to the both library teeth 512, 516. In one embodiment, when the user moves the library tooth 516 far away from the arch form (e.g., perpendicularly up or down and far enough from the arch form), the arch form may be broken and the library tooth 516 may be disconnected (or unpacked) from the other library teeth 514, 512 in the arch form.

Figure 5C:
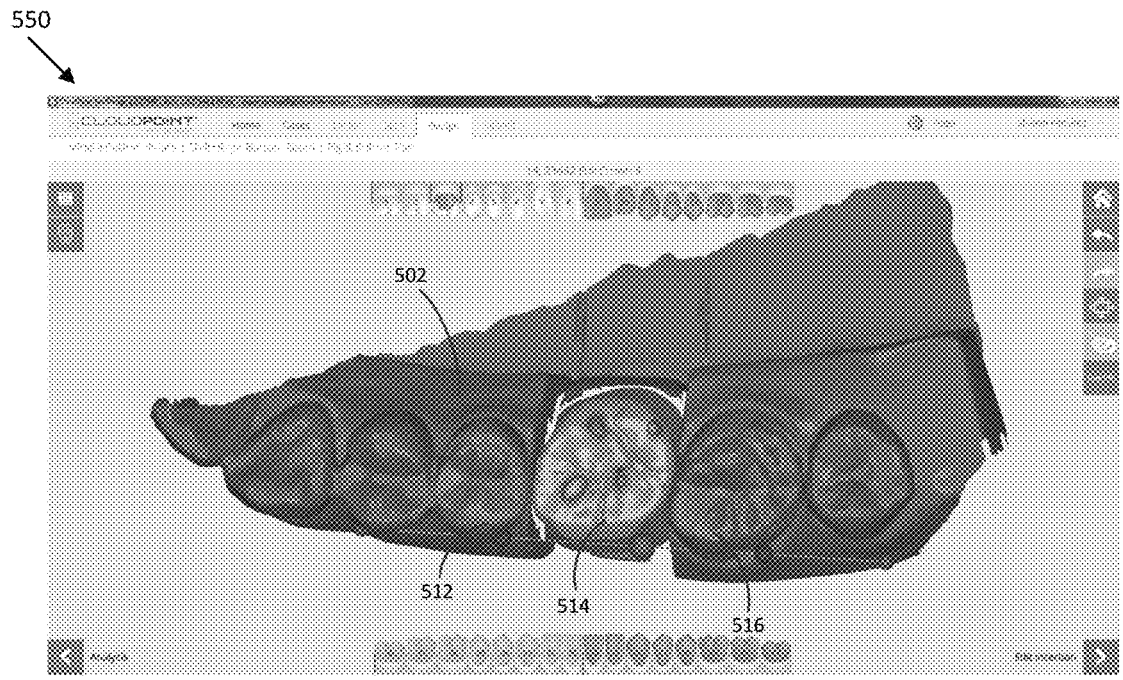
Figure 5D:
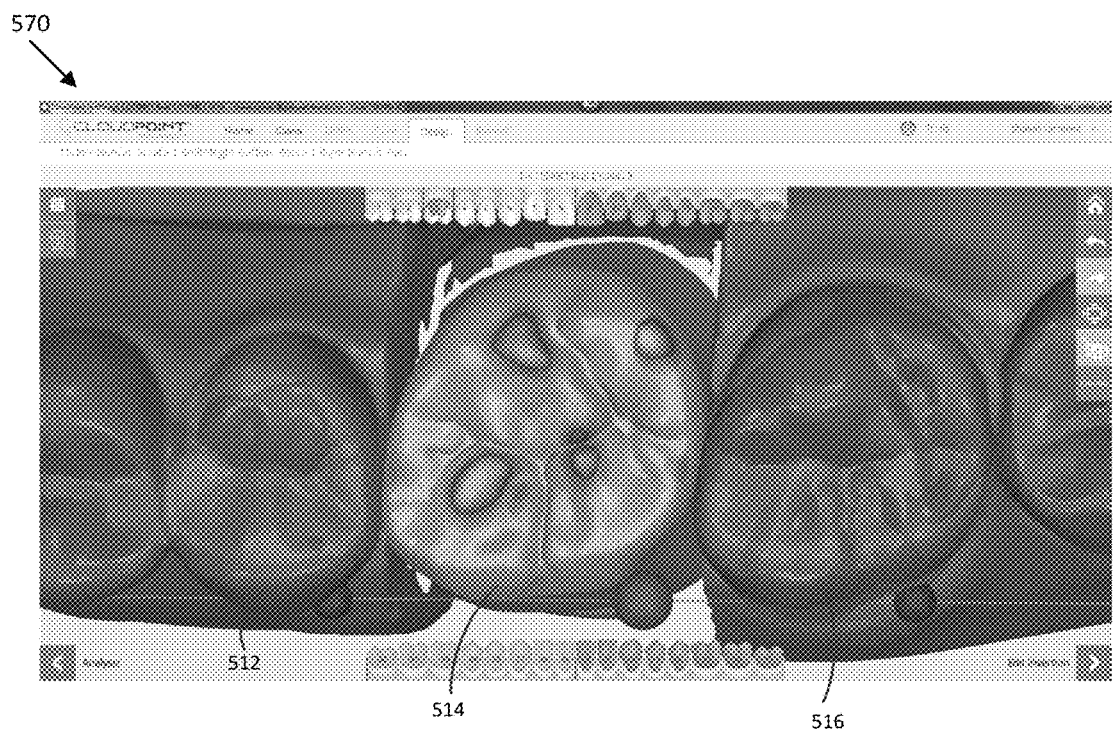

Referring to FIG. 5C, the user interface 550 shows the library tooth 516 is moved so as to be snapped to the scan data 502. The library teeth 512, 514, 516 pack to one another. Referring to FIG. 5D, a user interface 570 shows an enlarged and detailed representation of the arch form of the library teeth 512, 514, 516. From the user interface 570, it can be shown that the library teeth 512, 514, 516 in the arch are packed together and stay within zero contact distance to one another.

Figure 6A:
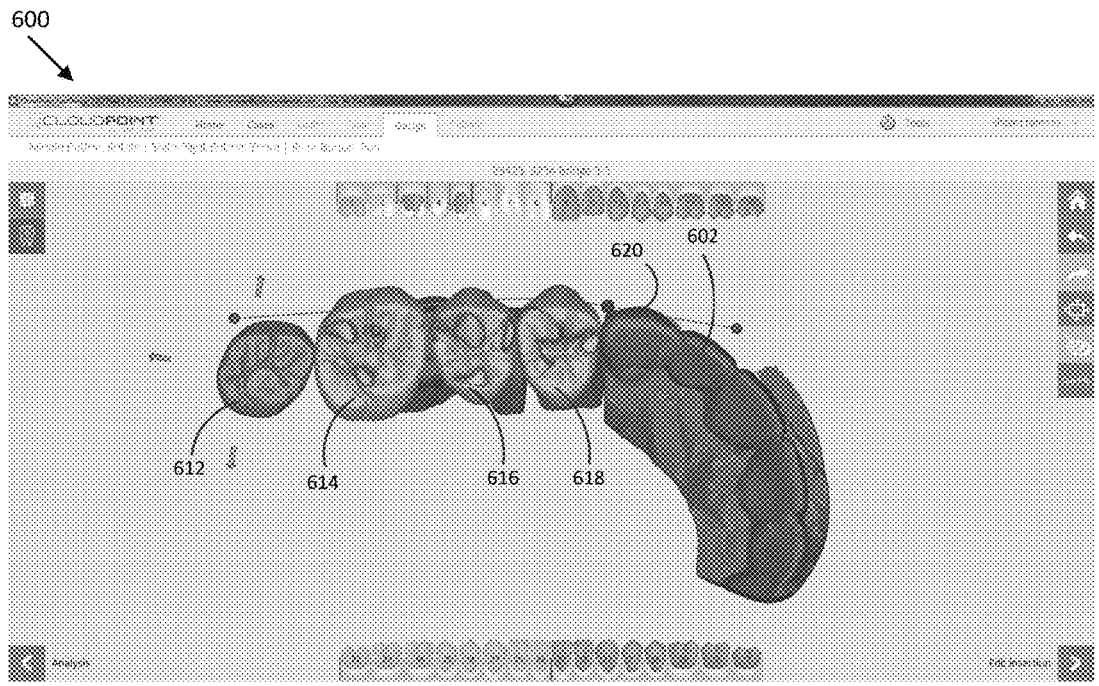
FIGS. 6A-6B are graphic representations of mesial packing effect in bridge design provided by a dental restoration design program according to one embodiment.
Figure 6B:
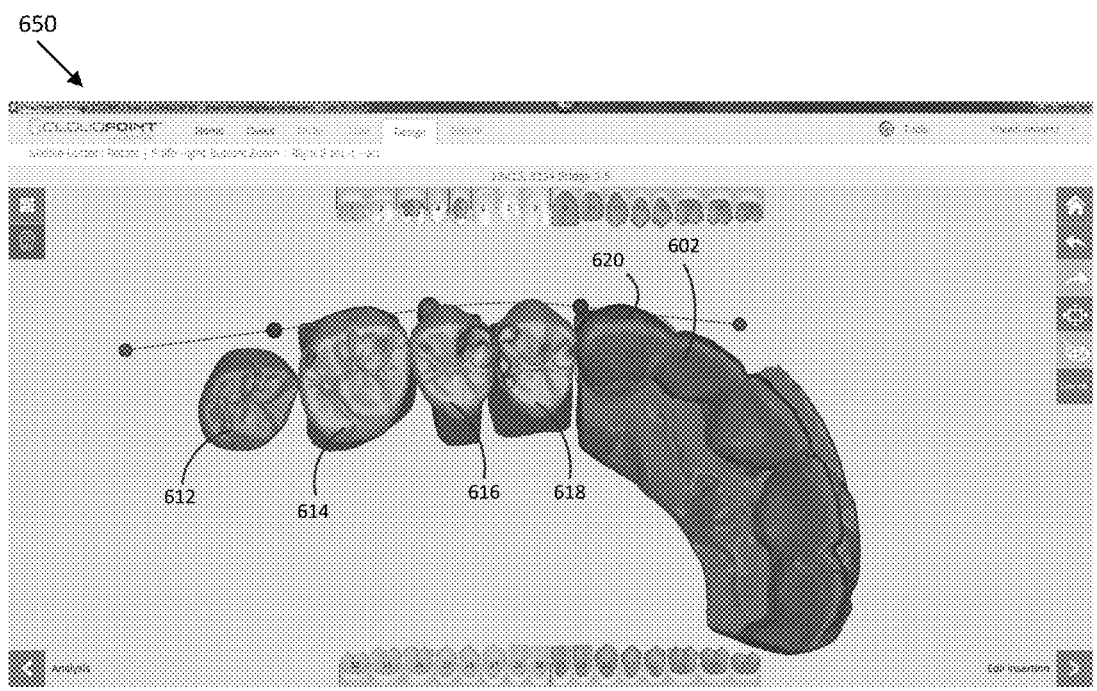

Referring now to FIGS. 6A-6B, mesial packing effect in bridge design provided by a dental restoration design program is depicted according to one embodiment. Referring to FIG. 6A, a user interface 600 includes scanned dentition data, as represented by element 602, and an arch form of library teeth, as represented by elements 612, 614, 616, 618, 620. The library teeth 612, 614, 616, 618, 620 are packed to one another and form the arch form. In one embodiment, the library teeth 614, 616, 618 may form a proposed bridge to be designed for the preparation teeth. In another embodiment, any of the library teeth 612, 614, 616, 618, 620 may form the bridge or represent other types of teeth in the patient's dentition. The library tooth 620 has been snapped to the scan data 602. The user can click and move the other tooth 612 to an appropriate position. During the moving of the tooth 612, the library teeth 614, 616, 618 may change in size, position, or both, for each of these teeth 614, 616, 618 to pack to one another and also pack to the neighboring teeth 612, 620. For example, as depicted in the user interface 650 in FIG. 6B, when the user moves the library tooth 612 towards the bridge of the teeth 614, 616, 618, each or any of the bridge teeth 614, 616, 618 shrink inward to the center point to pack to one another. In addition, when the tooth 612 is moving, the bridge teeth 614, 616, 618 may also move accordingly to pack to one another.

Figure 7A:
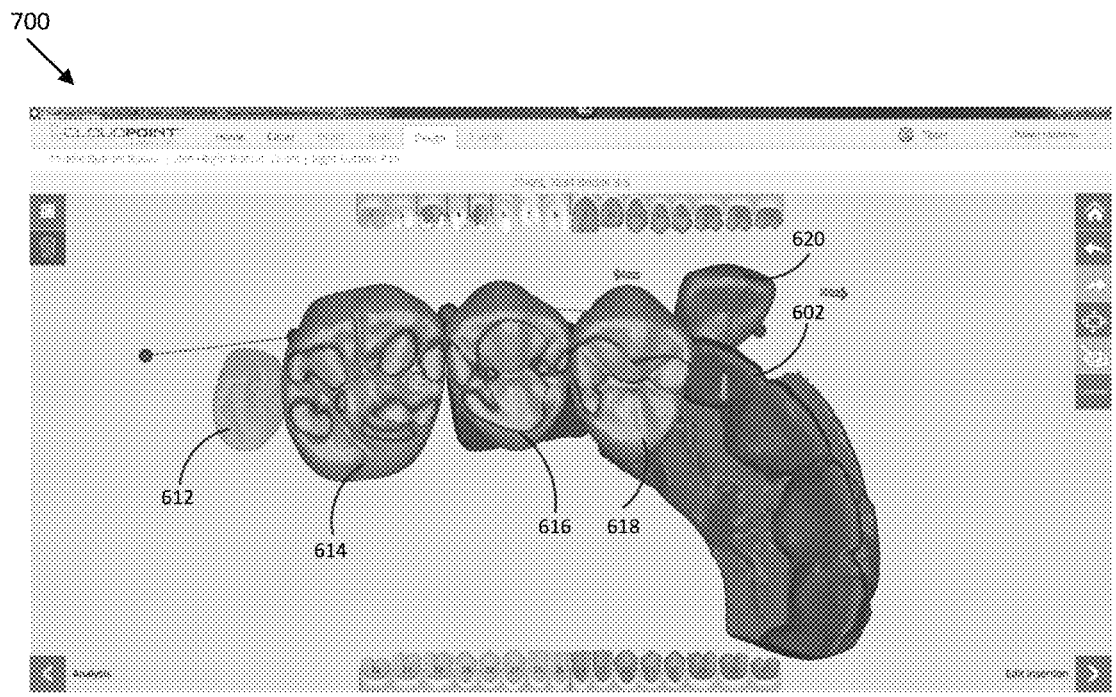
FIGS. 7A-7B are graphic representations of mesial packing during snapping in bridge design provided by a dental restoration design program according to one embodiment.
Figure 7B:
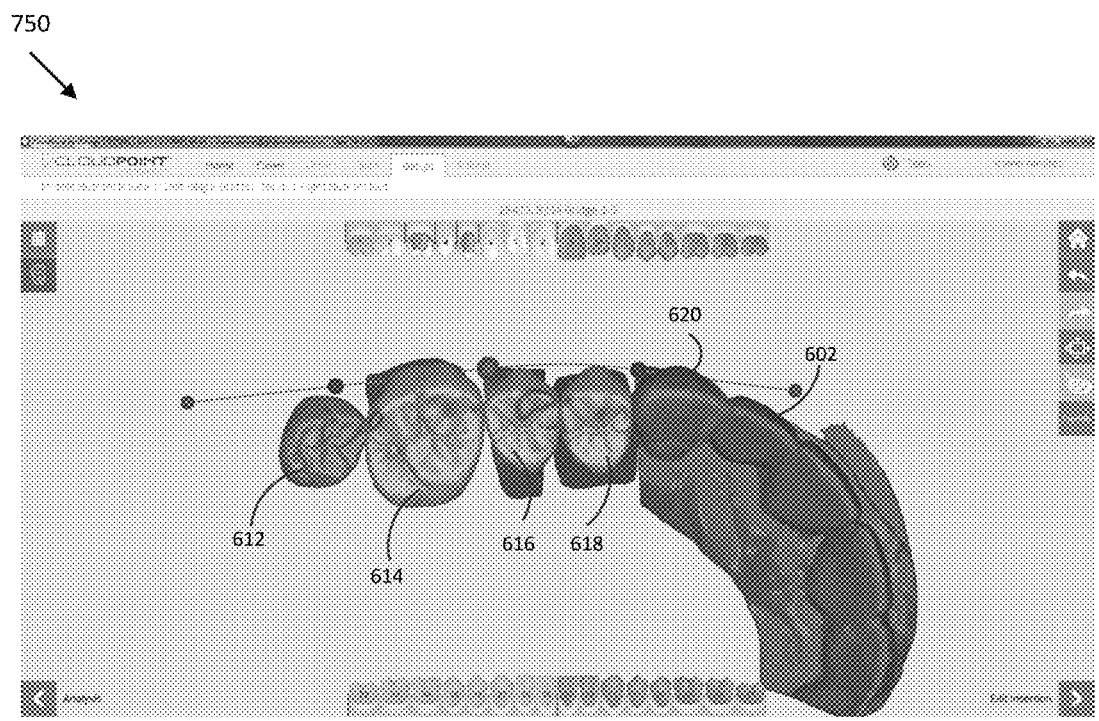

Referring now to FIGS. 7A-7B, mesial packing during snapping in bridge design provided by a dental restoration design program is depicted according to one embodiment. Referring to FIG. 7A, a user interface 700 includes the same elements 602, 612, 614, 616, 618, 620 as in user interface 600 in FIG. 6A. In the depicted user interface 700 in FIG. 7A, the library tooth 620 is not snapped to the scan data 602. The user can move the tooth 620 to snap to the scan data 602. During the moving of the tooth 620, the bridge of teeth 614, 616, 618 resize (e.g., shrink) to pack to the moving tooth 620. Additionally, the other tooth 612 may also move to pack to the bridge. Referring to FIG. 7B, a user interface 700 shows that the tooth 620 has been snapped to the scan data 602 and the other teeth in the arch form 612, 614, 616, 618 all pack to one another.

Figure 8A:
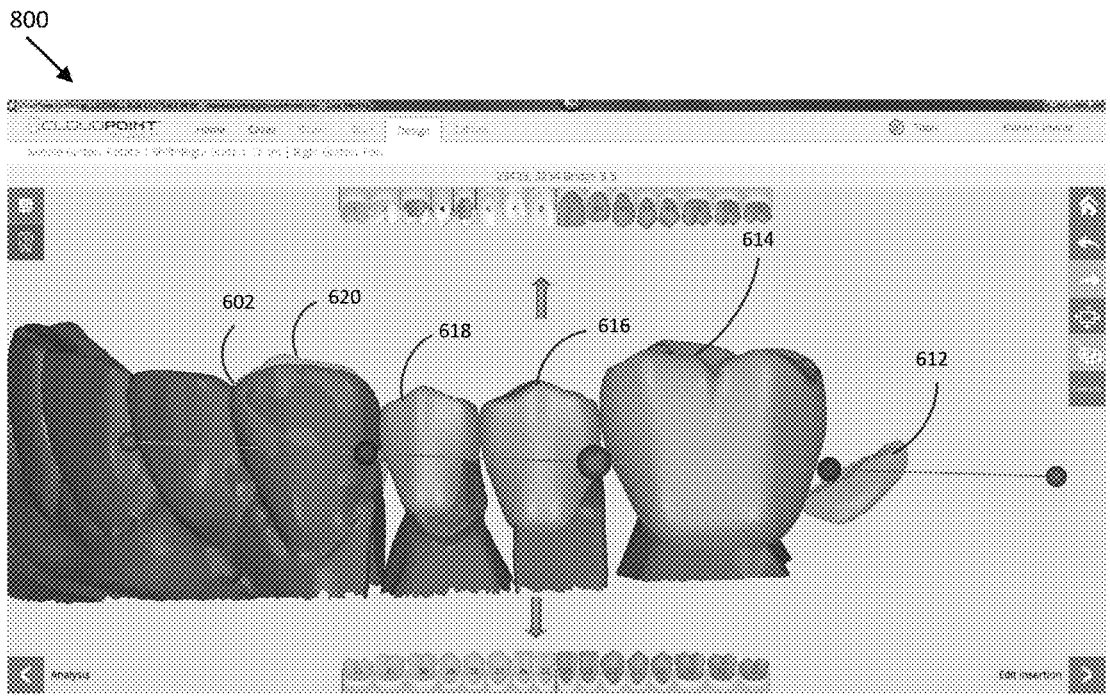
FIGS. 8A-8C are graphic representations of mesial packing effect in bridge design provided by a dental restoration design program according to another embodiment.
Figure 8B:
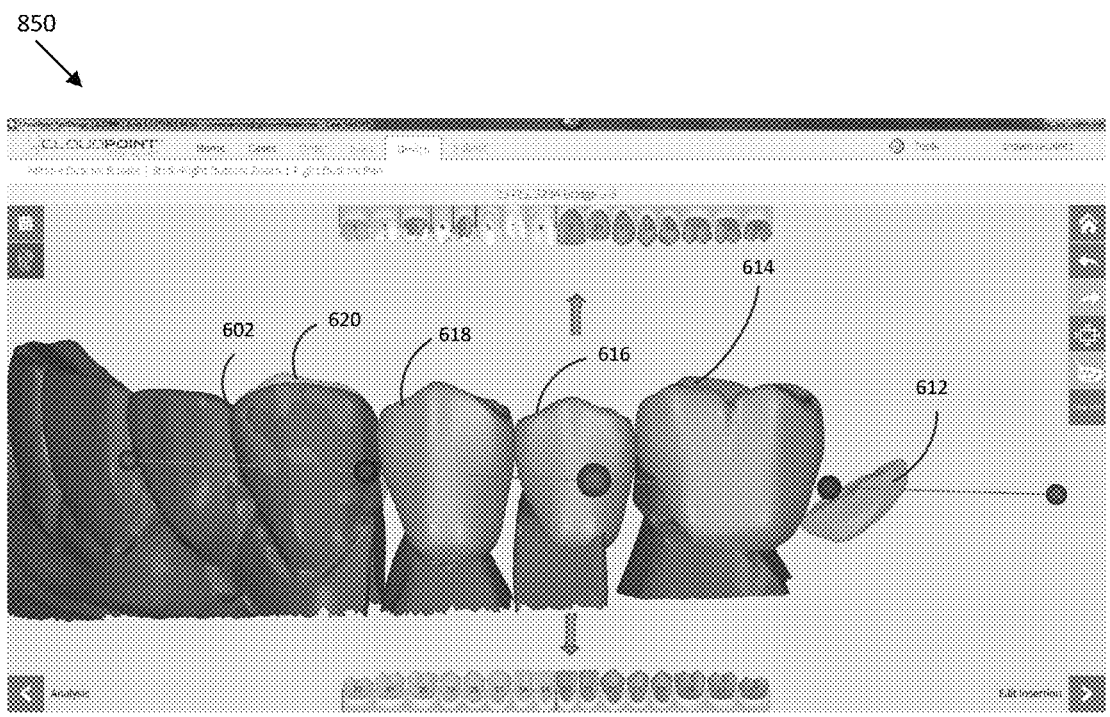
Figure 8C:
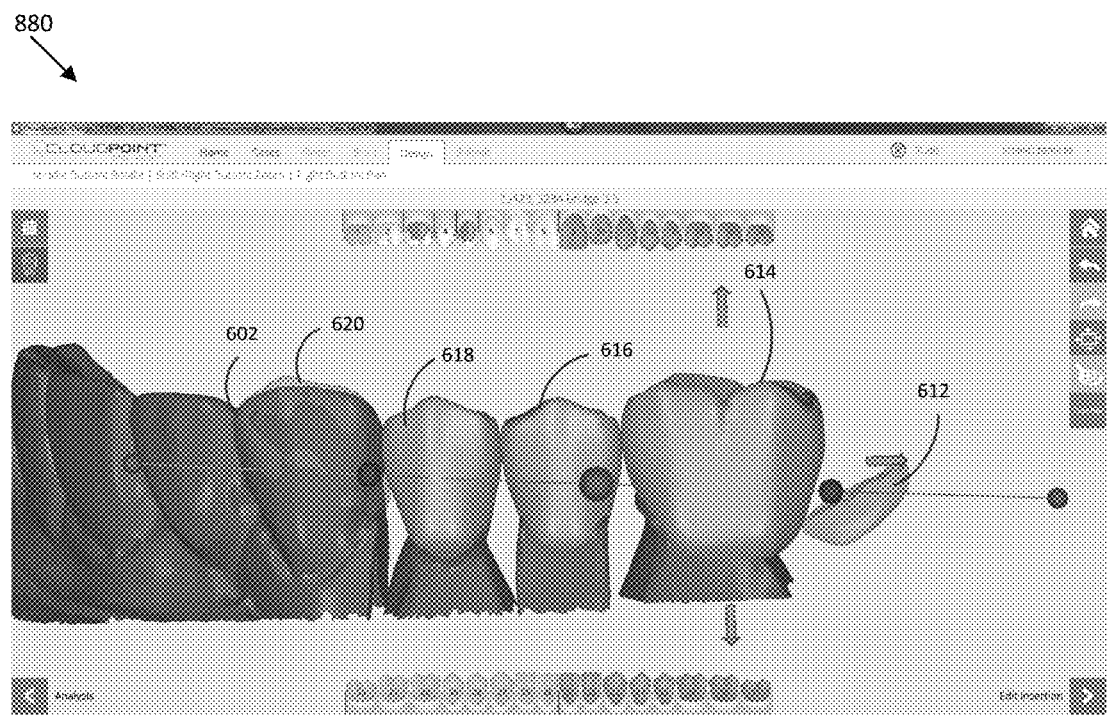

Referring now to FIGS. 8A-8C, mesial packing effect in bridge design provided by a dental restoration design program is depicted according to another embodiment. Referring to FIG. 8A, a user interface 800 includes the same elements 602, 612, 614, 616, 618, 620 as in user interface 600 in FIG. 6A. In the depicted user interface 800 in FIG. 8A, the tooth 620 is snapped to the scan data 602 (anchored) and therefore is represented as transparent. When the user is moving the bridge tooth 616 from left to right of the screen (e.g., away from the bridge tooth 618 and towards the bridge tooth 614), as depicted in a user interface 850 in FIG. 8B, the bridge teeth 614, 618 change their sizes accordingly to pack to their neighboring teeth respectively. For example, the bridge tooth 614 shrinks in its size to pack to the teeth 616, 612. On the other hand, the bridge tooth 618 expands in its size to pack to the teeth 616, 620. In some embodiments, the bridge teeth 614, 618 may also move accordingly so that the teeth 612, 614, 616, 618, 620 all pack to one another.

Referring to FIG. 8C, a user interface 880 shows that the bridge tooth 614 is expanded by the user to a bigger size and both the neighboring bridge teeth 616, 618 shrink to smaller sizes to keep packing to their neighboring teeth respectively. Additionally, tooth 612 moves aside to pack to the expanded bridge tooth 614.

Figure 9:
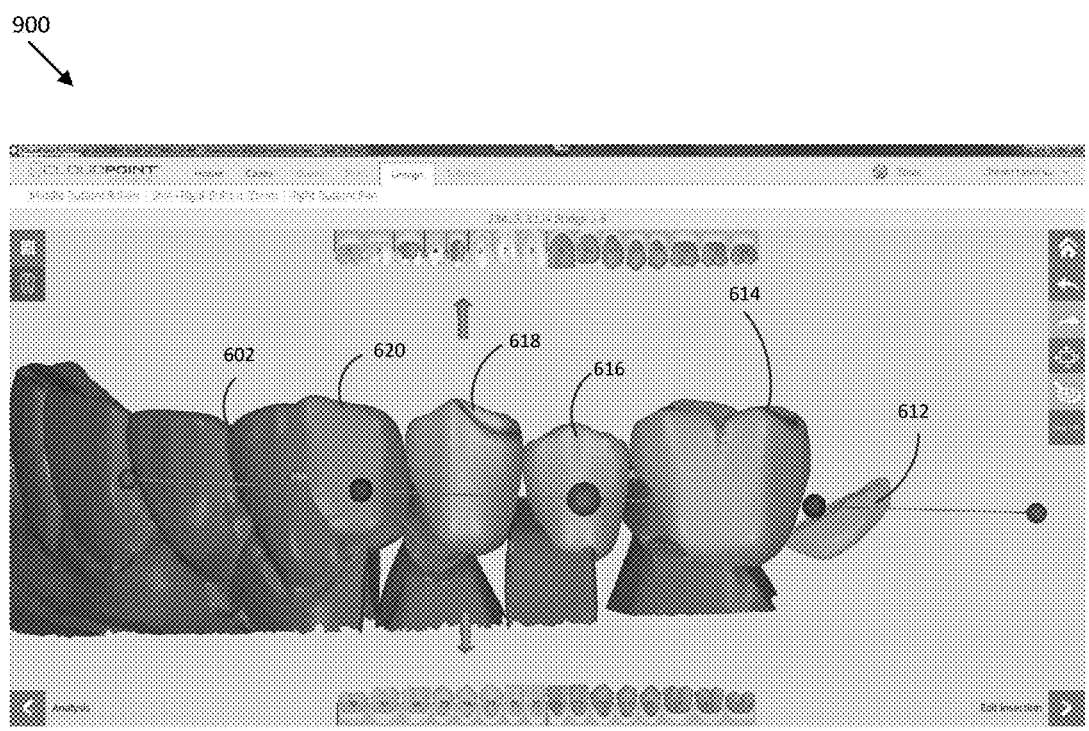
FIG. 9 is a graphic representation showing when anchoring is broken due to mesial packing according to one embodiment.

Referring now to FIG. 9, a user interface 900 showing when anchoring is broken due to mesial packing is depicted according to one embodiment. When the user moves and/or resizes the bridge tooth 618, the anchored neighboring tooth 620 (e.g., snapped to the scan data 602) has to move to pack to the bridge tooth 618. In some embodiments, when the user moves the bridge tooth 618 far enough or resizes the tooth 618 dramatically enough, in order to keep packing to the changed tooth 618 the anchored neighboring tooth 620 leaves the anchor position, for example, a position best matching the scan data 602, or resizes to a condition not matching the scan data 602. Thus, the anchor is broken.

Exemplary Dental Restoration Design System

Figure 10:
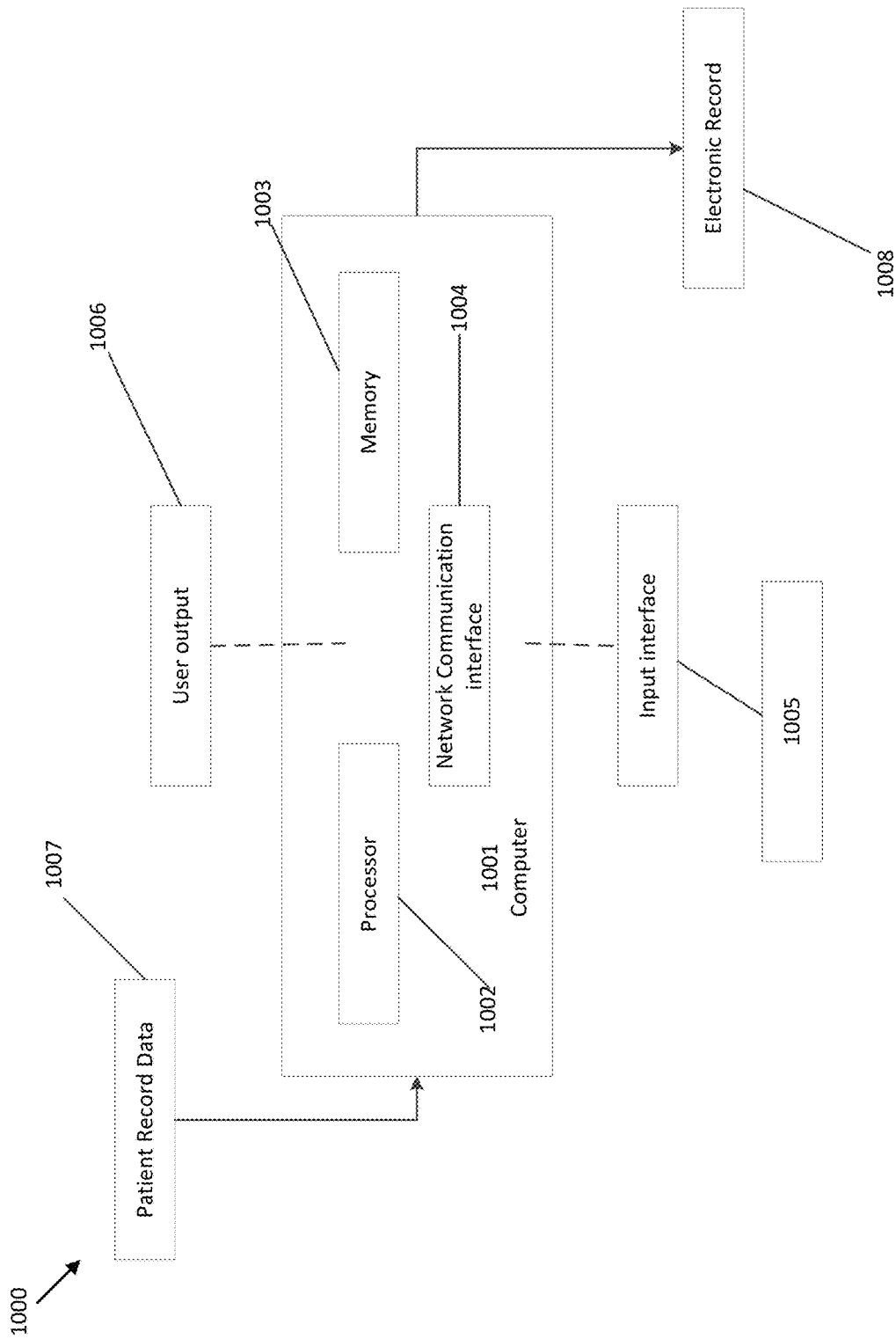
FIG. 10 is a block diagram of a dental restoration design system according to one embodiment.

Referring now to FIG. 10, a simplified block diagram of a dental restoration design system 1000 is described according to one embodiment. The system 1000 typically includes a computer 1001, which may comprise a microprocessor, integrated circuit, or other suitable computing device. The computer 1001 typically includes a processor 1002, a memory 1003, and a network or communication interface 1004. The processor 1002 communicates with a number of peripheral devices, including the memory 1003 and the communication interface 1004. The communication interface 1004 provides the capability of transmitting information over a communication network or other data processing systems. An input interface or module 1005 is electronically connected to the computer 1001. The input interface 1005 may comprise a keyboard, mouse, touch screen, stylus pad, foot pedal, joy stick, or other suitable user input interface. Other types of user interface input devices, such as voice recognition systems, may also be used. A user interface output device, such as a monitor 1006, is also provided. The interface output device may also include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

The memory 1003 maintains the basic programming, commands, and other software that provide the functionality of the system 1000. The memory 1003 typically includes a number of memories including a main random access memory (RAM) for storage of instructions and data during program execution and a read only memory (ROM) in which fixed instructions are stored. A file storage subsystem may provide persistent (nonvolatile) storage for program and data files, and typically includes at least one hard disk drive and at least one floppy disk drive (with associated removable media). There may also be other devices such as a CD ROM drive and optical drives (all with their associated removable media). Additionally, the system may include drives of the type with removable media cartridges. The removable media cartridges may, for example be hard disk cartridges or flexible disk cartridges. One or more of the drives may be located at a remote location, such as in a server on a local area network, in a cloud data center, or at a site on the Internet's World Wide Web.

Data in the form of a patient record 1007 from the intra-oral dental scanning system 100 is delivered to the dental restoration system computer 1001. In some embodiments, the patient record 1007 includes identification information and an electronic model of the patient's dentition, as described above. Once the restoration is designed, data in the form of an electronic record 1008 that includes the restoration design is delivered to a fabrication system, such as a mill, as described more fully below.

Exemplary Method

Figure 11:
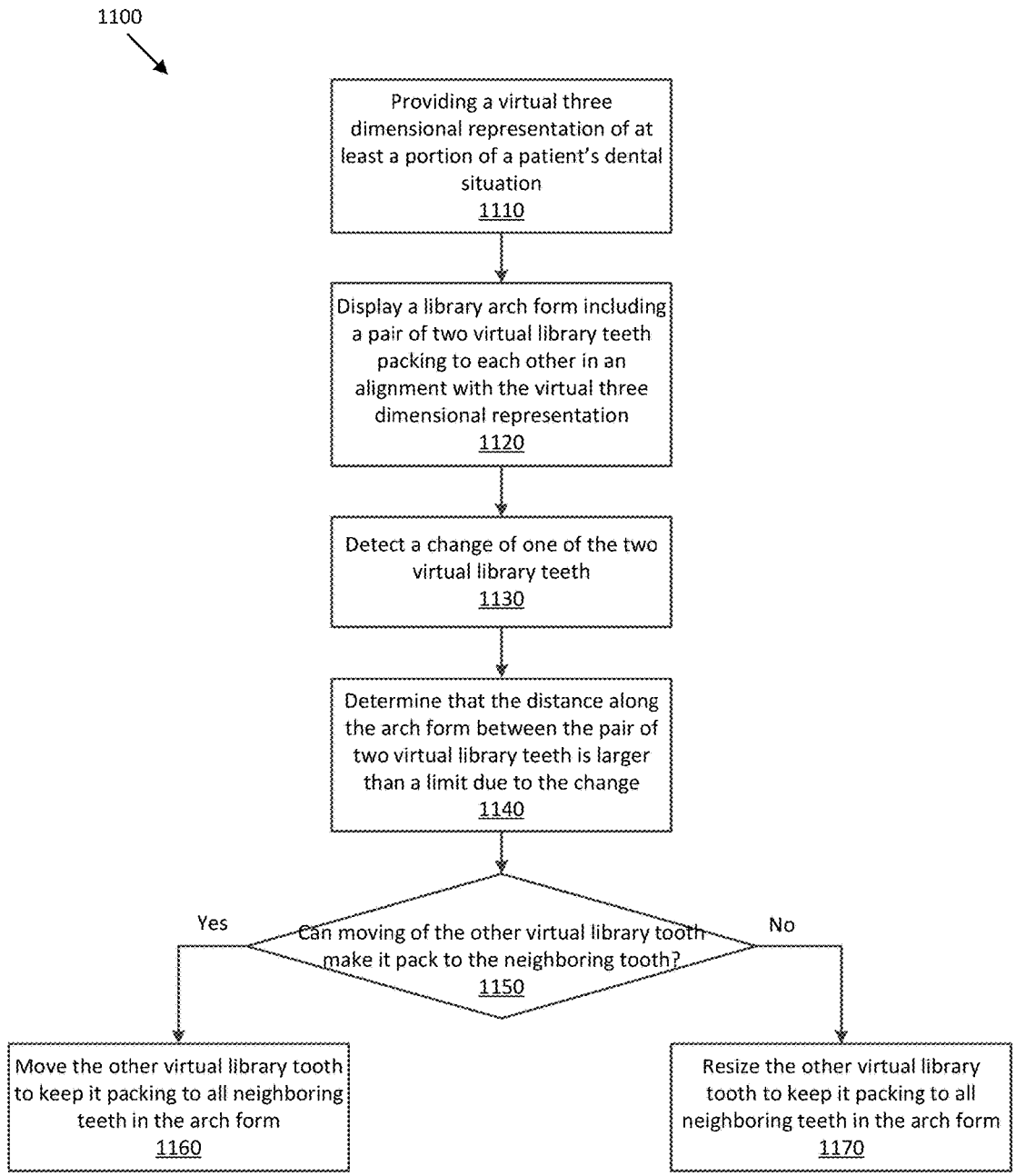
FIG. 11 is a flow diagram of a mesial packing process according to one embodiment.

FIG. 11 is a flow diagram of a mesial packing process 1100 according to one embodiment. FIG. 11 attributes the steps of the process 1100 to dental restoration design program, which may be stored in the memory 1003 of the dental restoration system computer 1001, when executed by the processor 1002, enables the computer 1001 to perform the mesial packing of the objects such as virtual library teeth or other dental imitations. However, some or all of the steps may be performed by other entities or modules. In addition, some embodiments may perform the steps in parallel, perform the steps in different orders, or perform different steps.

Initially, the dental restoration design program provides 1110 a virtual three dimensional (3D) representation of at least a portion of a patient's dental situation. For example, the dental restoration design program may receive scan data of the patient's dental situation and provide a virtual 3D representation of at least a portion of the patient's dental situation. The dental situation may include one or more teeth or other types of oral structure. The dental restoration design program displays 1120 a library arch form including a pair of two virtual library teeth packing to each other in an alignment with the virtual three-dimensional representation.

The dental restoration design program detects 1130 a change of one of the two virtual library teeth. The change may include, but not be limited to, moving, resizing (e.g., increasing or decreasing in size), rotation, etc. For example, when a user adjusts the position or size of a virtual library tooth in the arch form through a user device (such as a laptop, a smart phone, a personal computer, etc.), the dental restoration design program may detect the change of the virtual library tooth. In other examples, the dental restoration design program may also detect such a change of a virtual library tooth during a design proposal stage.

The dental restoration design program determines 1140 that the distance along the arch form between the pair of the two virtual library teeth is larger than a limit due to the change. For example, the dental restoration design program calculates the distance between the changed virtual library tooth and its neighboring tooth and determines if the distance is larger than a certain distance limit, e.g., a limit pre-defined by a user or an administrator of the program. For example, the user may pre-define the distance limit as zero. When the distance is larger than zero, the dental restoration design program determines that the distance between the pair of the two virtual library teeth is larger than the limit.

The dental restoration design program determines 1150 whether moving of the other virtual library tooth can make it pack to all neighboring tooth in the arch form. In one embodiment, the dental restoration design program may determine if there is any anchored end tooth in the arch form. If there is no anchored end tooth, then all other virtual library teeth can move freely to keep packing to one another. In another embodiment, the arch form may include more than two virtual library teeth. The dental restoration design program may then determine how many other virtual library teeth are in the arch form, how many other virtual library teeth are in the middle of the arch form, etc. The dental restoration design program may also determine the relative position of the other virtual library tooth in the arch form. Based on these determinations, the dental restoration design program can determine if moving of the other virtual library tooth is able to achieve the packing of all teeth in the arch form.

If the dental restoration design program determines that moving of the other virtual library tooth can make it pack to all neighboring teeth in the arch form, the dental restoration design program moves 1160 the other virtual library tooth to keep it packing to the all neighboring teeth in the arch form.

If the dental restoration design program determines that moving of the other virtual library tooth cannot make it pack to all neighboring teeth in the arch form, the dental restoration design program resizes 1170 the other virtual library tooth to keep it packing to all neighboring teeth in the arch form.

The above description is included to illustrate the operation of the preferred embodiments and is not meant to limit the scope of the invention. The scope of the invention is to be limited only by the following claims. From the above discussion, many variations will be apparent to one skilled in the relevant art that would yet be encompassed by the spirit and scope of the invention.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present invention be limited not by this detailed description, but rather by the claims of this application. As will be understood by those familiar with the art, the present invention may be embodied in other specific forms without departing from the spirit or essential characteristics thereof. Likewise, the particular naming and division of the modules, routines, features, attributes, methodologies and other aspects are not mandatory or significant, and the mechanisms that implement the present invention or its features may have different names, divisions and/or formats. Furthermore, as will be apparent to one of ordinary skill in the relevant art, the modules, routines, features, attributes, methodologies and other aspects of the present invention can be implemented as software, hardware, firmware or any combination of the three. Also, wherever a component, an example of which is a module, of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the present invention is in no way limited to implementation in any specific programming language, or for any specific operating system or environment. Accordingly, the disclosure of the present invention is intended to be illustrative, but not limiting, of the scope of the present invention, which is set forth in the following claims.

What is claimed is:

1. A computer-implemented method of designing a dental restoration at a display, the method comprising:
   providing a virtual three dimensional representation of at least a portion of a patient's dental situation;

displaying a library arch form in an alignment with the virtual three dimensional representation, the library arch form comprising at least three virtual library teeth, including a second and a third virtual library teeth each packing to a first virtual library tooth;
in response to a parametric change of the first virtual library tooth, moving the second virtual library tooth to keep packing to the changed first virtual library tooth;
anchoring the third virtual library tooth to a fixed status; and
in response to a parametric change of the second virtual library tooth, resizing the first virtual library tooth to keep packing to the second virtual library tooth,
wherein the first virtual library tooth also keeps packing to the third virtual library tooth, and
wherein a limit distance of packing is pre-defined by one selected from the group consisting of a dental restoration design program user and a dental restoration design program administrator.

2. The method of claim 1, wherein each pair of two virtual library teeth packing to each other are within a certain contact distance.

3. The method of claim 2, wherein the contact distance is measured by the closest point to point distance between the pair of virtual library teeth.

4. The method of claim 1, wherein the parametric change of the first virtual library tooth includes at least one of the following: moving in position, resizing, rotating and reshaping.

5. The method of claim 1, wherein the parametric change of the second virtual library tooth includes at least one of the following: moving in position, resizing, rotating and reshaping.

6. The method of claim 1, wherein a fourth virtual library tooth packs to the second virtual library tooth, and the method further comprising:
anchoring the fourth virtual library tooth to a fixed status; and
in response to a parametric change of the second virtual library tooth, resizing the first virtual library tooth to keep packing to the second virtual library tooth,
wherein the first virtual library tooth also packs to the third virtual library tooth and the second virtual library tooth also packs to the fourth virtual library tooth.

7. The method of claim 6, wherein the parametric change of the second virtual library tooth includes at least one of the following: moving in position, resizing, rotating and reshaping.

8. The method of claim 6, wherein responsive to the parametric change of the second virtual library tooth, the fourth virtual library tooth is moved to pack to the second virtual library tooth and the fixed status of the fourth virtual library tooth is lost.

9. A computer-implemented method of designing a dental restoration at a display, the method comprising:
providing a virtual three dimensional representation of at least a portion of a patient's dental situation;
displaying a library arch form in an alignment with the virtual three dimensional representation, the library arch form comprising at least two virtual library teeth, including a first virtual library tooth and a second virtual library tooth;
in response to a parametric change of the first virtual library tooth, moving the second virtual library tooth to keep packing to the changed first virtual library tooth;
wherein the library arch form also comprises a missing virtual library tooth with a gap between the first and second virtual library teeth and the two virtual library teeth both pack to the missing virtual library tooth with the gap, and the method further comprising:
in response to a parametric change of any one of the first and second virtual library teeth, moving the missing virtual library tooth with the gap to keep packing to the both of the first and second virtual library teeth, and
wherein a limit distance of packing is pre-defined by one selected from the group consisting of a dental restoration design program user and a dental restoration design program administrator.

10. The method of claim 9, wherein the parametric change of any one of the first and second virtual library teeth includes at least one of the following: moving in position, resizing, rotating and reshaping.

11. The method of claim 9, further comprising:
anchoring one of the pair of the first and second virtual library teeth to a fixed status;
in response to a parametric change of the other of the pair of the first and second virtual library teeth, resizing the missing virtual library tooth with the gap to keep packing to the both of the first and second virtual library teeth.

12. The method of claim 11, wherein the parametric change of the other of the pair of the first and second virtual library teeth includes at least one of the following: moving in position, resizing, rotating and reshaping.

13. The method of claim 9, wherein a third virtual library tooth packs to the other of the pair of the first and second virtual library teeth and the third virtual library tooth is snapped to a fixed status, and the method further comprising:
in response to a parametric change of the other of the pair of the first and second virtual library teeth, resizing the missing virtual library tooth with the gap to keep packing to the both of the first and second virtual library teeth.

14. The method of claim 13, wherein responsive to the parametric change of the other of the pair of the first and second virtual library teeth, the third virtual library tooth is moved to pack to the other of the pair of the first and second virtual library teeth and the fixed status of the third virtual library tooth is lost.

15. A non-transitory computer readable medium storing executable computer program instructions for designing a dental restoration at a display, the computer program instructions comprising instructions for:
providing a virtual three dimensional representation of at least a portion of a patient's dental situation;
displaying a library arch form in an alignment with the virtual three dimensional representation, the library arch form comprising at least three virtual library teeth, including a second and a third virtual library teeth each packing to a first virtual library tooth;
in response to a parametric change of the first virtual library tooth, moving the second virtual library tooth to keep packing to the changed first virtual library tooth;
anchoring the third virtual library tooth to a fixed status; and
in response to a parametric change of the second virtual library tooth, resizing the first virtual library tooth to keep packing to the second virtual library tooth,
wherein the first virtual library tooth also keeps packing to the third virtual library tooth, and
wherein a limit distance of packing is pre-defined by one selected from the group consisting of a dental restoration design program user and a dental restoration design program administrator.

16. A system for designing a dental restoration at a display, the system comprising:
- a processor; and
- a non-transitory computer-readable storage medium comprising instructions executable by the processor to perform steps comprising:
- providing a virtual three dimensional representation of at least a portion of a patient's dental situation;
- displaying a library arch form in an alignment with the virtual three dimensional representation, the library arch form comprising at least three virtual library teeth, including a second and a third virtual library teeth each packing to a first virtual library tooth;
- in response to a parametric change of the first virtual library tooth, moving the second virtual library tooth to keep packing to the changed first virtual library tooth;
- anchoring the third virtual library tooth to a fixed status; and
- in response to a parametric change of the second virtual library tooth, resizing the first virtual library tooth to keep packing to the second virtual library tooth,
- wherein the first virtual library tooth also keeps packing to the third virtual library tooth, and
- wherein a limit distance of packing is pre-defined by one selected from the group consisting of a dental restoration design program user and a dental restoration design program administrator.

* * * * *